United States Patent
Makarychev

(10) Patent No.: US 12,046,329 B2
(45) Date of Patent: Jul. 23, 2024

(54) EFFICIENT PAYLOAD EXTRACTION FROM POLYNUCLEOTIDE SEQUENCE READS

(71) Applicant: MICROSOFT TECHNOLOGY LICENSING, LLC, Redmond, WA (US)

(72) Inventor: Konstantin Makarychev, Chicago, IL (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1478 days.

(21) Appl. No.: 16/003,013

(22) Filed: Jun. 7, 2018

(65) Prior Publication Data

US 2019/0377851 A1    Dec. 12, 2019

(51) Int. Cl.
G16B 40/00    (2019.01)
G16B 30/00    (2019.01)
G16B 50/00    (2019.01)

(52) U.S. Cl.
CPC ............. *G16B 40/00* (2019.02); *G16B 30/00* (2019.02); *G16B 50/00* (2019.02)

(58) Field of Classification Search
CPC ........ G16B 30/00; G16B 50/00; G16B 30/10; G16B 40/00
USPC .......................................................... 706/13
See application file for complete search history.

(56) References Cited

U.S. PATENT DOCUMENTS

2016/0191076 A1* 6/2016 Leighton ............. H03M 7/3062
                                                               707/693

OTHER PUBLICATIONS

Ruslan Kalendar, Bekbolat Khassenov, Yerlan Ramankulov, Olga Samuilova, Konstantin I. Ivanov: "FastPCR: An in silico tool for fast primer and probe design and advanced sequence analysis". Genomics, 109 (2017) 312-319 (Year: 2017).*

Yu, B., Zhang, C. (2011). In Silico PCR Analysis. In: Yu, B., Hinchcliffe, M. (eds) In Silico Tools for Gene Discovery. Methods in Molecular Biology, vol. 760. Humana Press. (Year: 2011).*

(Continued)

*Primary Examiner* — Russell S Negin
*Assistant Examiner* — Guozhen Liu
(74) *Attorney, Agent, or Firm* — Benjamin Keim; Newport IP, LLC

(57) ABSTRACT

Systems and techniques for extracting information-containing payloads from DNA or other polynucleotides are provided. Decoding the sequence of payload regions from multiple polynucleotides to obtain encoded information includes sequencing the molecules with a polynucleotide sequencer. Reads generated by the polynucleotide sequencer can include information from multiple different sources mixed together. Primer sequences present in the reads identify which reads contain information from the same source. A computationally efficient technique for finding primer sequences in the reads includes comparing hashes of the reads and hashes of primer sequences to find an approximate location then computing edit distances between the primer sequences and the reads to find an exact location. Reads that include the same primer sequences may be clustered together. Sequences of the payload regions are extracted based on the locations of the primer sequences.

10 Claims, 7 Drawing Sheets

Specification includes a Sequence Listing.

(56) References Cited

OTHER PUBLICATIONS

Kirill Rotmistrovsky, Wonhee Jang, Gregory D. Schuler, A web server for performing electronic PCR, Nucleic Acids Research, vol. 32, Issue suppl_2, Jul. 1, 2004, pp. W108-W112. (Year: 2004).*
Tabatabaei Yazdi, SM Hossein, et al. "A rewritable, random-access DNA-based storage system." Scientific reports 5.1 (2015): 14138. (Year: 2015).*
Zhang, Haowen, et al. "Fast and efficient short read mapping based on a succinct hash index." BMC bioinformatics 19 (2018): 1-14. (Year: 2018).*
Mohamadi, Hamid, et al. "ntHash: recursive nucleotide hashing." Bioinformatics 32.22 (2016): 3492-3494. (Year: 2016).*
"Extract Sequence from Fasta Using Primer", Retrieved From: https://www.biostars.org/p/216039/, Dec. 15, 2017, 4 Pages.
"International Search Report and Written Opinion Issued in PCT Application No. PCT/US19/033638", dated Dec. 11, 2019, 16 Pages.
Bornholt, et al., "A DNA-Based Archival Storage System", Proceedings of the Twenty-First International Conference on Architectural Support for Programming Languages and Operating Systems, Mar. 25, 2016, pp. 637-649.
Communication pursuant to Article 94(3) received in EP No. 19730622.8, mailed on Apr. 3, 2024, 5 pages.
Silva, et al., "New Trends of Digital Data Storage in DNA", BioMed Research International, vol. 2016, Sep. 5, 2016, 15 pages.

\* cited by examiner

```
                         SEQUENCE LISTING

<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: illustrative synthetic sequence

<400> SEQUENCE: 1
cgcatagcga agctggcatc tggaca                                          26
```

EFFICIENT PAYLOAD EXTRACTION FROM POLYNUCLEOTIDE SEQUENCE READS

BACKGROUND

Polynucleotides such as deoxyribose nucleic acid (DNA) are an emerging data storage technology that has the promise of providing unprecedented density and durability. Data, such as but not limited to binary data, is encoded in synthetic polynucleotide molecules. The sequence of polynucleotide bases (e.g., adenine (A), cytosine (C), guanine (G), and thymine (T)) can represent the original sequence of 1's and 0's in the binary data. Due to limits on the length of polynucleotide molecules that can by synthesized, a given set of source data (e.g., a computer file) may be split across a large number of polynucleotide molecules. A polynucleotide sequencer reads the sequences of the polynucleotide molecules. The sequence data, or "reads," generated by the polynucleotide sequencer may be output in a file that contains sequence data which corresponds to multiple different sets of source data.

The output from the polynucleotide sequencer identifies the order of bases in the polynucleotide molecules. However, reads corresponding to multiple different sets of source data may be mixed together. Furthermore, there may be errors in polynucleotide synthesis (i.e., the molecule actually synthesized has a different sequence of polynucleotides than intended), degradation during storage of a polynucleotide molecule (i.e., damage that changes its sequence), and errors in sequencing (i.e., the sequence reported by the polynucleotide sequencer is different than the actual sequence of the molecule). The errors may cause insertions, deletions, and substitutions to the sequence of nucleotides in a read. Thus, the output of the polynucleotide sequencer may include a large number of undifferentiated and noisy reads.

There are many steps involved in retrieving the original data from the output of the polynucleotide sequencer. One of those steps is identifying which reads encode a particular set of source data (i.e., grouping the reads that contain data from a particular computer file and excluding reads with data from other files). This is challenging due to the mixing of the reads, the presence of errors in the reads, and the large volume of data.

SUMMARY

Grouping reads associated with the same set of source data can be referred to as "pre-clustering" because there may be subsequent clustering of reads for reasons described in U.S. provisional patent application No. 62/402,873 entitled "Efficient Clustering Of Noisy Polynucleotide Sequence Reads." Pre-clustering can group all reads from the polynucleotide sequencer output into multiple sets of reads each associated with a different set of source data. For example, if several billion DNA strands are used to store the data for five-thousand Ultra-HD video files, pre-clustering can separate the reads from the billion DNA strands into 5000 clusters each containing a large number of separate reads that store data for a single one of the video files. Thus, in some implementations, pre-clustering begins with a very large number of noisy polynucleotide reads and processes the reads to recover sets of reads that correspond only to data from one or more of the sets of data (e.g., files). Techniques to decode and reconstruct the data encoded in the set of clustered reads are described in U.S. patent application Ser. No. 15/004,827 entitled "Error Correction For Nucleotide Data Stores," U.S. patent application Ser. No. 15/427,344 entitled "Primer Design For Retrieval Of Stored Polynucleotides," U.S. patent application Ser. No. 15/459,268 entitled "Random Access Of Data Encoded By Polynucleotides," and U.S. patent application Ser. No. 15/536,115 entitled "Trace Reconstruction From Noisy Polynucleotide Sequencer Reads."

The synthetic polynucleotide molecules used to store the source data may be designed so that two primer binding sites flank a stretch of the polynucleotide which encodes the source data. A primer is a short strand of RNA (ribonucleic acid) or DNA generally about 18-22 bases in length that serves as a starting point for polynucleotide synthesis. Primers are used for many techniques in biochemistry and molecular biology such as polymerase chain reaction (PCR). The primer binding sites are regions of the polynucleotide molecules with a reverse complementary base sequence to which primers anneal. This portion of the polynucleotide molecule that contains the source data (e.g., A's, G's, C's, and T's representing 1's and 0's) can be referred to as the "payload." The primers can be paired so that two primer sites, one forward and one reverse, with different sequences are always used together. The sequences of the primers and the forward/reverse pairing of primers is known because the polynucleotide molecules are deliberately designed and synthesized. Unique primers may be used for all payloads corresponding to a given set of source data. For example, all the DNA strands containing pieces of the same video file may be designed and synthesized to bind with the same forward primer and reverse primer. If, as mentioned above, there are 5000 video files stored together in a physically undifferentiated set of DNA strands, then there can be 5000 forward primers and 5000 reverse primers. Therefore, the polynucleotide sequences of the primers provide information that is used to extract and group payload sequences from the reads. If the polynucleotide molecules are designed and synthesized so that there is a 1:1 correlation between a primer and a single set of source data, then identification of a primer sequence or the reverse complement of a primer sequence in a read also identifies the associated payload as part of the source data.

However, errors change the sequences of some of the primer sequences reported in the reads generated by a polynucleotide sequencer. The types of errors can include nucleotide insertions, deletions, and substitutions. The presence of errors limits the usefulness of exact matching. It is also possible that a single read may contain sequence data from multiple different polynucleotide molecules. Thus, in one read there may be a large number of payloads from the same or different sources. Each of these multiple payloads may be surrounded by a pair of primers. Approximate string matching is used to identify primer sequences in the reads that do not have identical sequences to any of the known primers. Approximate string matching (also referred to as fuzzy string searching) is a technique for finding strings that match a pattern approximately rather than exactly. However, many approximate string matching techniques can be very computationally expensive which creates practical difficulties such as limiting system throughput when processing a billion different strings of polynucleotide sequence data.

Before performing approximate string matching, exact matches may be identified. Even though errors can be introduced at many stages, in some implementations there may be reads that contain accurate primer sequences. Techniques that can be used to identify exact matches include determining if a primer sequence is a substring of a read or building a deterministic finite automaton (DFA) that checks if any of the known primer sequences are substrings of any of the reads. Exact matching can be performed quickly with relatively low computational cost.

Prediction strategies may be used to limit the size of strings evaluated by approximate string matching. The intentional design of the polynucleotide molecules and characteristics of the manipulations performed during synthesis, storage, and/or sequencing can suggest regions of a read that are likely to contain a primer sequence. For example, if a first primer sequence is identified, and the expected length of the payload region is also known, then the likely position of a second primer sequence can be inferred by adding (or subtracting) the payload length. Also, modifications to the polynucleotide molecule as synthesized may indicate where along the read a primer sequence is expected. Additionally, reads may include a given number of nucleotides before the forward primer sequence and/or after the reverse primer sequence. Thus, primer sequences may be expected, for example, 10 nucleotides after the start (or before the end) of a read. Statistics collected from prior recognition of primer sequences may be used to identify typical or expected locations of primer sequences. For example, if polynucleotide molecules designed and processed in a particular way may tend to have the forward primer sequence between 15 and 20 bases from the start of the read and the reverse primer binding site sequence between 155 to 160 bases past the end of the first primer sequence. Knowledge of this structure enables prediction of locations in a read that are likely to contain a primer sequence. These locations can be checked first. Checking a smaller portion or a read uses less computing power than checking the entire read.

If a primer sequence is identified either by exact matching or by using a prediction strategy to narrow the region for searching, then the location of the primer sequence in the read can be stored and further computationally expensive operations may be avoided.

Approximate string matching may be performed to identify portions of the reads that do not exactly match any of the primer sequences. A technique for identifying primer sequences in the reads through approximate matching includes using a hash function to identify approximate locations followed by calculating edit distances over limited portions of the reads ("evaluation windows") identified by the approximate locations. This technique is less computationally expensive than performing naïve edit distance calculations across the entire population of reads because a match between hash functions can be computed much faster than edit distances and because the evaluation windows over which edit distances are calculated are much shorter than the entire length of the reads.

The hash function $h(x)$ satisfies three conditions that allow it to approximate the results of edit distance calculations at lower computational cost. First, if the edit distance between two polynucleotide sequences x and y of length L (e.g., the length of a primer) is small, then the distance between $h(x)$ and $h(y)$ is also small. Thus, if the hash of, for example, a primer sequence and a hash of a portion of a read are similar, then the edit distance between the actual sequences (not the hashes) is also similar. Second, if the edit distance between x and y is large, then the distance between $h(x)$ and $h(y)$ is large with high probability. Thus, if two polynucleotide sequences are dissimilar, then the hashes of those two sequences will likely be dissimilar as well. Third, a small shift in the portion of a read being hashed requires only small computational effort to compute the new hash value. For example, if the hash of base pairs (bp) 20-40 in a read is known then the hash of bp 21-41 can be found quickly. Stated differently, given the hash value $h(a\#x)$ (where x is a polynucleotide sequence (e.g., a substring of a read), a and b are two arbitrary polynucleotide values (e.g., A, G, C, or T), $h(a\#x)$ and $h(x\#b)$ are concatenations of a and x, and x and b respectively), the value of $h(x\#b)$ can be computed quickly. Furthermore, given the distance between $h(a\#x)$ and $h(y)$, the distance between $h(x\#b)$ and $h(y)$ can also be found quickly. One way to obtain a hash with these properties is to use k-mer embedding and count the k-mers in the hash.

The hash function may be applied to some or all of the substrings in a read that are the same length as a primer. For example, if a read is 200 bp long and the primer is 20 bp long (a primer binding site is the same length as the primer) then a hash may be calculated for each 20 bp substring in the read. The polynucleotide sequence of the read can be represented as string s and the hash $h(x)$ may be computed for each substring x of s of length L, where L is the length of the primer. After a hash is computed for the first substring of s (e.g., the first or last 20 bp of a read) hashes of other substrings may be computed by dynamically updating $h(x)$ based on a one-bp shift in the portion of the read being hashed (e.g., computing the hash of bp 2-22 by updating the hash of bp 1-21 rather than computing the hash of bp 2-22 entirely anew).

The hash $h(P_i)$ may be computed for some or all of the primers and compared to the hashes of the substrings of the read. Thus, the hashes for some or all of the primer binding sites sequences known to be used in a particular set of polynucleotide molecules may each be compared to all of the substrings of the same length as the primers in the reads generated by a polynucleotide synthesizer. The comparison may be a calculation of distance between a pair of hashes. Distances between hashes may be calculated in many ways including Hamming distance and $L_1$ distance. If the distance between $h(x)$ and $h(P_i)$ is small (less than a certain threshold) that may be recorded as an approximate match. The value of the threshold may be tuned by a user during searching and/or developed based on performance of past searches.

The approximate match is a match between hashes not between actual polynucleotide sequences. The subsequence of the read that corresponds to the matching hash $h(x)$ may be evaluated for an actual match by calculating the edit distance to the primer sequence. Because the comparison of hashes only identifies an approximate location, the polynucleotides corresponding to the closest hash may not have the smallest edit distance (i.e., best match) to the actual primer sequence. Thus, an evaluation window in the read which is longer than the subsequence identified by the matching hash is evaluated to find the subsequence with a smallest edit distance. The evaluation window includes the polynucleotide sequence corresponding to the closest hash and additional polynucleotide sequences on one or both sides. Thus, the evaluation window allows portions of the read in the vicinity of the approximate match to be evaluated for the best match.

Identification of the primer sequences in the reads (even when the sequences in the reads are not exact matches to the actual primer sequences) enables identification of the set of source data (e.g., a computer file) that a payload sequence encodes. Pre-clustering of the reads, or portions of reads, based on same primers groups all the reads that contain parts of the same set of source data.

The reads may include additional sequence data that represents sequencing and/or synthesis artifacts in addition to the primer sequences and the payload sequences. Because it is the payloads that contain the information is used to reconstruct the original source data, the payload sequences may be extracted from other sequences in the reads. Recall that polynucleotide molecules may be designed and synthesized so that a primer sequence is directly adjacent to each end of a payload region. Once primer sequences are identified and located in the reads, the payload sections of the reads can be identified as the string of polynucleotide bases between two primer sequences. The exact locations of the primer sequences as determined by edit distance delineate the payload regions. The result is multiple payload sequences (i.e., strings of A's, G's, C's, and T's) that are all associated with the same primers/source data. The association may be made by appending metadata to the payloads, placing the payload sequences in a look-up table, storing clustered payload sequences in a same location, or by another technique.

Once there is a collection of clustered payloads that have been extracted from the non-payload portions of the reads, further assembly and decoding operations such as those described in one or more of the patent applications referenced above may be performed to regenerate the original data. For example, each set of clustered and extracted payloads may be processed to decode the nucleotide base sequences and create binary data such as a computer file.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s), method(s), computer-readable instructions, module(s), algorithms, hardware logic, and/or operation(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
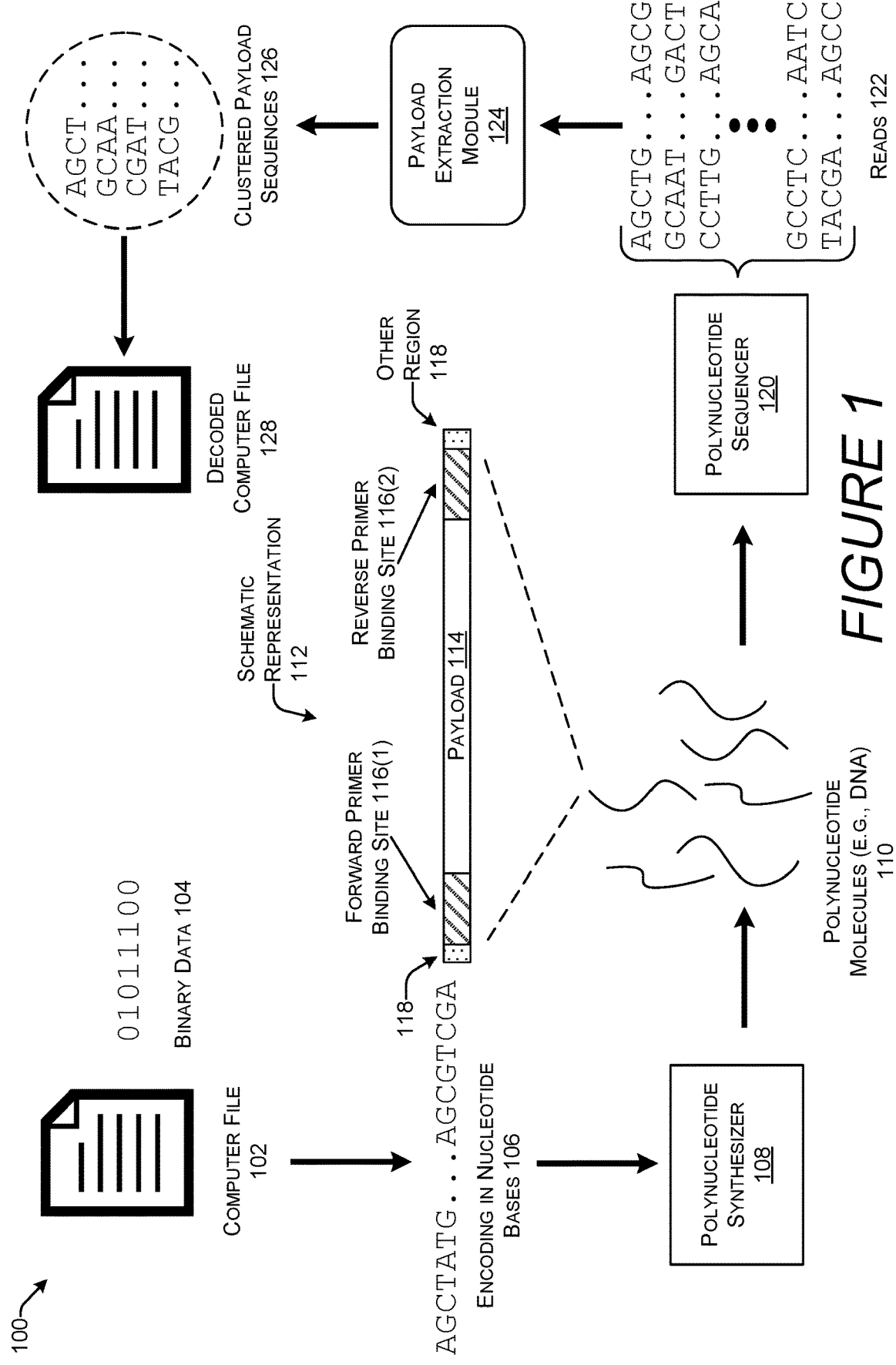
FIG. 1 shows a schematic representation of a system creating and clustering polynucleotide reads.

FIG. 1 illustrates a schematic representation of a system 100 for clustering reads that contain information or data from the same computer file 102 or another original source. The source information may be in any format such as printed text in a book and is not limited to a computer file 102. If the source information is a computer file 102 then the original data may be binary data 104. The binary data 104 is encoded in a representation using nucleotide bases 106. Naturally occurring DNA includes four nucleotide bases: adenine (A), cytosine (C), guanine (G), and thymine (T). A DNA strand is a linear sequence of these nucleotide bases. The two ends of a DNA strand, referred to as the 5' and 3' ends, are chemically different. DNA sequences are conventionally represented starting with the 5' nucleotide end at the left. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus the two sequences are the "reverse complement" of each other. Two strands do not need to be fully complementary to bind to one another. Ribonucleic acid (RNA) has a similar structure to DNA and naturally occurring RNA consists of the four nucleotides A, C, G, and uracil (U) instead of T. Ribonucleic Acid (RNA) has the base uracil (U) instead of thymine. Unnatural bases such as dNaM and dTPT3 may also be used. Use of unnatural bases may expand the alphabet so that there can be five, six, or more possible bases used for the encoding. Fewer than all available natural bases may be used so that the alphabet could also consist of fewer than four possible bases. "Polynucleotide" as used herein includes DNA and RNA with both natural bases and/or unnatural bases. An example encoding may use the bases AGC to represent the letter "a" or the bases "TG" to represent the bit "0". Thus, the original source information is encoded in a string of nucleotide bases. If the encoding scheme is known, the sequence of the polynucleotide can be decoded to recover the original binary data 104. Moreover, other polymers besides DNA or RNA that are able to be amplified and sequenced in an analogous manner may also be used with the techniques disclosed herein.

The representation using nucleotide bases 106 provides an encoding of the original binary data 104 in a format that can be stored in polynucleotide molecules. Thus, this provides a way to store data in polynucleotides. There are multiple possible techniques for encoding binary data 104, or other data, as a string of A's, G's, C's, T's, U's, and/or unnatural bases. The contributions provided by this disclosure work equally well with any encoding scheme. Polynucleotides may be designed to include sequences of nucleotides that perform a role other than encoding binary data 104. For example, sequences that bind to primers may be added to facilitate manipulation of polynucleotides through biochemical techniques that use on primer binding. Unique identifying sequences, analogous to bar codes, may also be added.

Once the desired sequences of the polynucleotide molecules are established, a polynucleotide synthesizer 108, creates the actual polynucleotide molecules 110. Polynucleotide synthesizers 108, also called oligonucleotide synthesizers, perform chemical synthesis of polynucleotides by joining nucleosides in a specified sequence. This specified sequence is determined in part by the encoding in nucleotide bases 106. The nucleosides assembled by a polynucleotide synthesizer 108 can be normal or modified nucleosides which have protecting groups to prevent their amines, hydroxyl groups, and phosphate groups from interacting incorrectly. One phosphonamidite is added at a time, the 5' hydroxyl group is deprotected and a new base is added and so on. With current polynucleotide synthesis technology, the chain grows in the 3' to 5' direction, which is backwards relative to natural biosynthesis. At the end, any protecting groups are removed. Being a chemical process, it is possible for incorrect interactions to occur leading to defective products. The longer the polynucleotide sequence that is being synthesized, the more defects there are, thus with current technology this process is only practical for producing relatively short sequences of nucleotides. The current practical limit is about 200 bp (base pairs) for a polynucleotide with sufficient quality. The length limitations of polynucleotide synthesizers 108 is one factor considered during the design of the polynucleotide sequences. Even polynucleotide molecules 110 that are shorter than the practical limits of polynucleotide synthesizers 108 contain some errors. Thus, for some of the polynucleotide molecules 110, the actual sequence of the nucleotides is not the same as intended sequence.

Thus, in an implementation the polynucleotide molecules 110 produced by the polynucleotide synthesizer 108 may be about 180-200 bp long and contain errors. Polynucleotide molecules 110 containing data from many different sources (e.g., different computer files 102) may be stored together. The polynucleotide molecules 110 can be stored in any number of physical formats such as in an aqueous solution, as a dried pellet, etc. If polynucleotide molecules 110 are mixed this way during storage, it may be necessary to separate the encoded data according to data source prior to decoding. The separation may be performed by physically separating the polynucleotide molecules 110 and/or by using information contained in the polynucleotide molecules 110 to identify which data belongs to a given computer file 102.

A schematic representation 112 of a single polynucleotide molecule 110 illustrates a possible organizational structure. This organization structure may be at least partially designed intentionally. The polynucleotide molecules 110 are double-stranded (or possibly single-stranded) molecules that may be linear or circularized. The total length of a single polynucleotide molecule 110 may be constrained by the limits of the polynucleotide synthesizer 108. Thus, this schematic representation 112 may, for example based on current polynucleotide synthesis technology, represent a length of 200 bp or less. Out of that total length, there is a payload 114 which comes from the encoding of nucleotide bases 106 and represents a portion of the original binary data 104. Millions of payloads 114 (and thus millions of polynucleotide molecules 110) may be used to encode an entire computer file 102. The organizational structure, and thus the polynucleotide molecule 110, may also include primer binding sites 116 such as forward primer binding site 116(a) and a reverse primer binding site 116(b). The primer binding sites 116 may be located adjacent to both ends of the payload 114. Thus, the nucleotides corresponding to the payload 114 can be identified by their location between two paired primer binding sites 116. Once the primer binding sites 116 are known, the location of the payload 114 is known. The primer binding sites 116 are locations on the polynucleotide molecules 110 to which a primer can bind through reverse-complementary base pairing. Primers are short, synthetic strands of DNA or RNA, that anneal to one or more of the polynucleotide molecules 110 due to complementary base paring. Typically, primers are between 18-22 bp long but shorter and longer primers are possible. In in implementation, most or all of the primers used for a given set of polynucleotide molecules 110 may have the same length. Perfect complementary base paring in not necessary for primers to function; primers with a few unpaired bases can still anneal. The polynucleotide molecules 110 may also include other regions 118 shown in the schematic representation 112 at the ends of the molecule. However, the other regions 118 may be located at places besides the ends. The other regions 118 may contain "random" or "junk" sequences that do not encode information and are not primer binding sites 116. The other regions 118 may be artifacts added at some point during the creation or processing of the polynucleotide molecules 110. The other regions 118 may be added to protect the ends of the polynucleotide molecules 110 or for another reason.

The schematic representation 112 may represent, for example, a total length of 200 bp. This length may vary based on the capabilities of the polynucleotide synthesizer 108. As mentioned above, the forward primer binding site 116(a) and the reverse primer binding site 116(b) may both be 20 bp long. The other regions 118 may together have a length of 30 bp. Thus, the payload region may be limited to a length of about 130 bp. This length can store 130 base-4 (or potentially more if unnatural bases are also used) units of information. Thus, to encode some computer files 102, or other original sources of data, millions of synthetic polynucleotides are needed.

The forward primer binding site 116(a) and the reverse primer binding site 116(b) may serve as locations for polymerase chain reaction (PCR) primers to anneal. PCR may be used to create multiple copies of the polynucleotide molecule. During PCR, the strands of a double-stranded polynucleotide are separated, and each serves a template for assembling a complementary strand. A PCR reaction has three main components: the template, primers, and enzymes. The template is a single- or double-stranded molecule (e.g., polynucleotide molecule 110) containing the sequence that will be amplified. The primers provide a starting point for nucleoside polymerization and define the beginning and end of the region to be amplified. The enzymes include polymerases and thermostable polymerases such as DNA polymerase, RNA polymerase and reverse transcriptase. The enzymes create double-stranded DNA from a single-stranded template by "filling in" complementary nucleotides one by one through addition of nucleoside triphosphates, starting from a primer bound to a template. PCR happens in "cycles," each of which doubles the number of templates in a solution. The process can be repeated until the desired number of copies is created. Multiple copies of the polynucleotide molecules 110 may be created in order to produce a sufficient quantity of sample for sequencing.

All of the copies of the original polynucleotide molecule 110 have the same nucleotide sequence as the original except for any errors introduced by the PCR amplification process. PCR amplification can cause errors due to misincorporation of nucleotides by DNA polymerase. PCR is a technique that involves many (often 20-30) rounds of a reaction to synthesize new copies of DNA. The errors that occur during PCR can occur during any round of the DNA synthesis reaction, so a PCR error can result in a large number of DNA fragments with a given error if the polymerase misincorporates a base during an early round of synthesis or can result in a small number of DNA fragments with errors if the polymerase misincorporates a base a later round of synthesis. The error rate of PCR is typically much lower than the error rate for other steps in the processes such as synthesis and sequencing.

The polynucleotide molecules 110 may be designed and synthesized so that all payloads 114 associated with the same source data have the same forward primer binding site 116(a) and/or the same reverse primer binding site 116(b). With this design, PCR amplification can be used to selectively increase the number of copies of the polynucleotide molecules 110 with primer binding sites 116 that correspond to the primers present during PCR. There may be a 1:1 correspondence between primer sequences and data sources.

Thus, each set of primers may be associated with a different computer file 102. This design provides random access by allowing selective amplification of only those polynucleotide molecules 110 associated with a particular computer file 102 or other source data. Although the polynucleotide molecules 110 that do not bind to the primers remain after PCR, they are present in a much lower concentration than the polynucleotide molecules 110 amplified by PCR. Thus, a polynucleotide sequencer 120 may not detect the polynucleotide molecules 110 that are not amplified.

PCR amplification using multiple different sets of primers in the same reaction, multiplex-PCR, is also possible. Multiplex-PCR will amplify polynucleotide molecules 110 that have primer binding sites 116 for any one of the sets of primers included in the multiplex-PCR. For example, ten different pairs of primers may be used together in multiplex-PCR to amplify the polynucleotide molecules 110 corresponding to ten different computer files 102. Thus, the polynucleotide molecules 110 for the ten different computer files 102 will be amplified relative to other polynucleotide molecules 110 but will still be mixed with each other. Separating the payloads 114 for each of the ten computer files 102 can be performed at a later stage by a technique other than PCR.

Some or all of the polynucleotide molecules 110 are provided to a polynucleotide sequencer 120 to determine the sequences of the nucleotides present in the polynucleotide molecules 110. The polynucleotide sequencer 120 reads the order of the nucleotide bases in a given polynucleotide molecule 110. Polynucleotide sequencing includes any method or technology that is used to determine the order of the bases—A, G, C, and T or U—in a strand of DNA or RNA. A base call represents a determination of which of the four nucleotide bases—A, G, C, and T (or U)—in a strand of DNA (or RNA) is present at a given position in the strand. Given the convention of representing DNA nucleotides with the letters A, C, G, and T, the reads 122 generated by a polynucleotide sequencer 120 are text strings that comprise the letters A, C, G, and T. Some reads 122 may include metadata describing characteristics of the read such as a confidence level for the accuracy of individual base calls in the read. Reads 122 may also contain other letters representing uncertainty in a base call, for example, International Union of Pure and Applied Chemistry (IUPAC) has an established set of single-letter codes to represent ambiguity in a DNA sequence. The reads 122 themselves may be in any suitable format such as plain text, FASTQ, EMBL, and FASTA.

Polynucleotide sequencers 120 use a variety of techniques to interpret molecular information and may introduce errors by failing to faithfully read the molecular structure. Each position in a read is an individual base call determined by the polynucleotide sequencer 120 based on properties sensed by components of the polynucleotide sequencer 120. The properties sensed by the polynucleotide sequencer 120 vary depending on the specific sequencing technology used. Sometimes the base calls are wrong. This is a source of error introduced by sequencing. Errors from sequencing are introduced at rates of a few percent to several tens of percent depending on the sequencing technology. This is several orders of magnitude greater than errors from PCR.

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5'- and 3'-ends of the fragments. DNA fragments that are attached to the surface of flow cell channels are extended and bridge amplified. The fragments become double stranded, and the double stranded molecules are denatured. Multiple cycles of solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, an image is captured, and the identity of the first base is recorded. The 3' terminators and fluorophores from each incorporated base are removed and the incorporation, detection, and identification steps are repeated. Sequencing-by-synthesis has a relatively low error rate (e.g., less than 1%) and produces read lengths of a few hundred base pairs. This length is generally sufficient to read the entire length of a single synthetic polynucleotide.

Another a sequencing technique that can be used is nanopore sequencing. A nanopore is a small hole of the order of one nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a polynucleotide molecule 110 passes through a nanopore, each nucleotide on the polynucleotide molecule 110 obstructs the nanopore to a different degree. Thus, the change in the current passing through the nanopore as the polynucleotide molecule 110 passes through the nanopore represents a reading of the polynucleotide sequence. Nanopore sequencing has much higher error rates (e.g., over 10%) than sequencing-by-synthesis. However, the read lengths of Nanopore sequencing are much longer—up to 800,000 bp long.

The polynucleotide sequencer 120 provides raw sequence data output referred to herein as polynucleotide reads or simple "reads" 122 that contain a string of letters representing the order of nucleotides detected by polynucleotide sequencer 120. The reads 122 contain noise introduced in part by errors of the polynucleotide sequencer 120. Some of the reads 122 may also include concatenation of two or more separate polynucleotide molecules 110. Thus, a single read 122 may include multiple payloads 114 and multiple sets of primer binding sites 116.

In an implementation, the polynucleotide sequencer 120 may process batches of unrelated polynucleotide molecules 110 during a single run. This may be done to efficiently use the full capacity of the polynucleotide sequencer 120. However, this can result in the reads 122 output by the polynucleotide sequencer 120 containing data from a mix of different original sources. Thus, even after selective PCR amplification, the results of multiple separate PCR products may be combined in a batch for sequencing. Therefore, the reads 122 output by the polynucleotide sequencer 120 may include sequences that came from multiple different computer files 102.

One task that can be performed by the payload extraction module 124 is separation of the reads 122 into multiple groups or "buckets" such that each bucket contains only reads with payloads 114 from the same original source such as the same computer file 102. The number of target buckets may be known or unknown prior to the clustering. A second task that can be performed by the payload extraction module 124 is identification of portions of the reads that contain the payload regions. Identification of the payloads 114 allows for extraction of the subsequence(s) of each read 122 from the subsequences corresponding to primer binding sites 116 and other regions 118.

Grouping the reads 122 into buckets is based on one or more subsequences in the reads 122 that are indicative of the source of binary data 104 encoded by the payloads 114. As mentioned above, one indicator may be the primer binding sites 116. For example, primer binding site 116 may have the example sequence CGATCGGAT and may be used in the design of all polynucleotide molecules 110 that contain a portion of the computer file 102 Summer_day.mp4. Other indicators of the data source may also be included in the design of the polynucleotide molecules 110. For example, a source tag may be included between the forward primer binding site 116(a) and the payload 114 (or in another location).

Clustering based on a subsequence of the reads 122 is challenging because of the large number of reads 122 to analyze. There may be millions or billions of reads 122 in a data set particularly if the output from multiple polynucleotide sequence 120 runs are analyzed together. It is also challenging because even though the identifying sequences such as primer binding sites 116 are known, those sequences will likely be imperfectly represented in the reads 122 due to errors at some point in the process. A technique used by the payload extraction module 124 to improve computational efficiency is finding approximate primer sites based on hashes then using edit distance to find the exact primer sites within the approximate location (rather than applying edit distance to the entire read 122). Illustrative hashing techniques and illustrative use of edit distance calculations are discussed in greater detail below.

The payload extraction module 124 can provide one or more sets of clustered payload sequences 126 from the reads 122. A set of clustered payload sequences 126 represents a grouping in which all or most of the payload sequences that each respectively encode part of same original binary data 104. Recall that the payloads 114 are the portions of the polynucleotide molecules 110 that encode the original binary data 104. When the payload sequences that in aggregate encode all of the original binary data 104 are grouped together, the nucleotide sequences of those payloads 114 can be decoded and the binary data 104 may be re-created and properly assembled resulting in a decoded computer file 128. There may be some errors in one or more parts of the data storage and recovery process. Thus, it is possible that the decoded computer file 128 does not have identical binary data as the original computer file 102. However, error correction techniques and use of redundancy greatly reduce the likelihood of any errors in the decoded computer file 128. Techniques for converting the clustered payload sequences 126 into the decoded computer file 128 are provided elsewhere and not discussed further in this disclosure.

Figure 2:
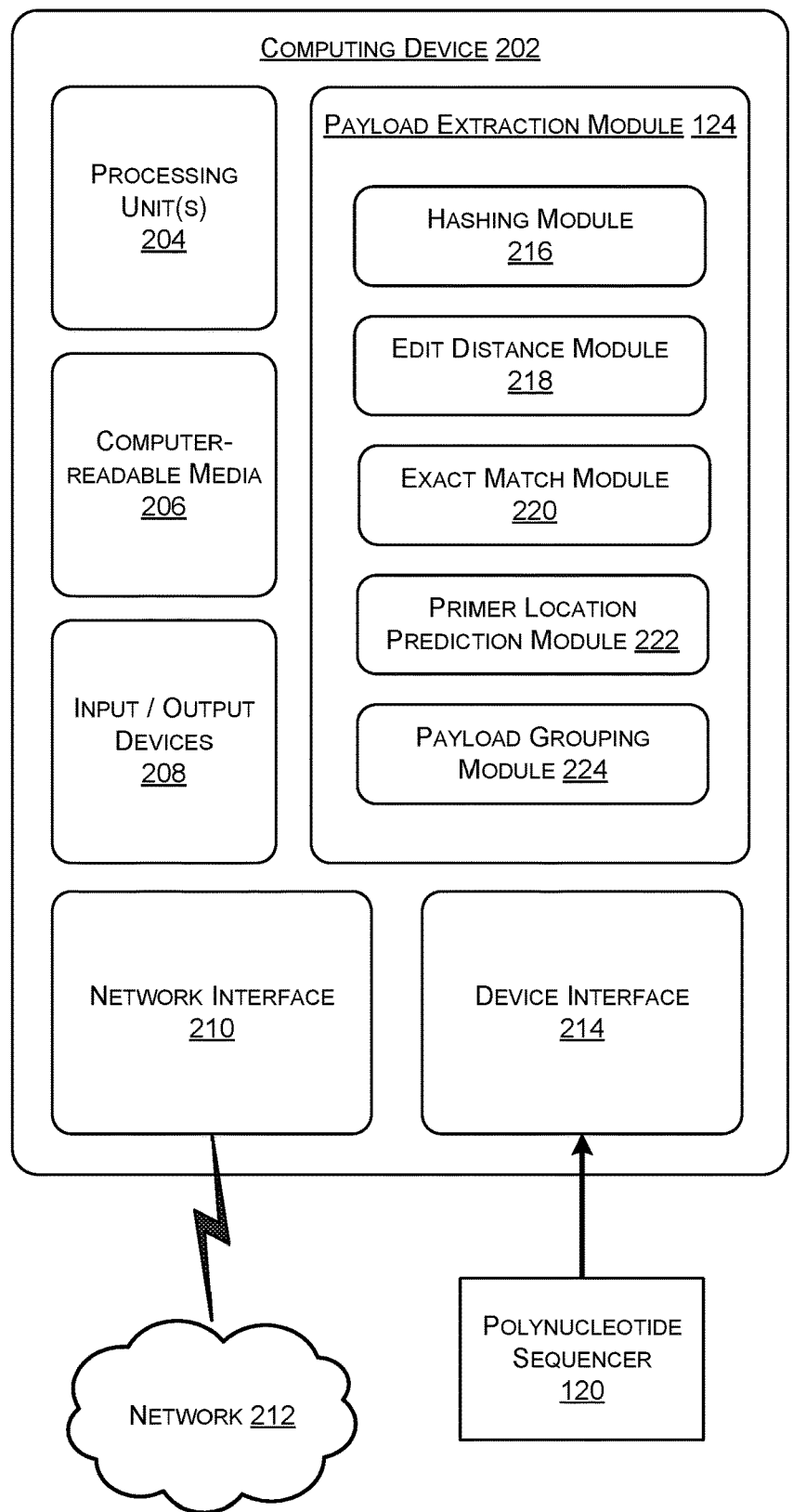
FIG. 2 shows a block diagram of an illustrative computing device for implementing the techniques of this disclosure.

FIG. 2 shows a block diagram 200 of an illustrative computing device 202 that may contain the payload extraction module 124 introduced in FIG. 1. The computing device 202 may be implemented with one or more processing unit(s) 204 and computer-readable media 206, both of which may be distributed across one or more physical or logical locations. The processing unit(s) 204 may include any combination of central processing units (CPUs), graphical processing units (GPUs), single core processors, multi-core processors, processor clusters, application-specific integrated circuits (ASICs), programmable circuits such as Field Programmable Gate Arrays (FPGA), and the like. In one implementation, one or more of the processing units(s) 204 may use Single Instruction Multiple Data (SIMD) or Single Program Multiple Data (SPMD) parallel architectures. For example, the processing unit(s) 204 may include one or more GPUs or CPUs that implement SIMD or SPMD. One or more of the processing unit(s) 204 may be implemented in software and/or firmware in addition to hardware implementations. Software or firmware implementations of the processing unit(s) 204 may include computer- or machine-executable instructions written in any suitable programming language to perform the various functions described. Software implementations of the processing unit(s) 204 may be stored in whole or part in the computer-readable media 206.

Alternatively or additionally, the functionality of computing device 202 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The computer-readable media 206 of the computing device 202 may include removable storage, non-removable storage, local storage, and/or remote storage to provide storage of computer-readable instructions, data structures, program modules, and other data. Computer-readable media 206 includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory, solid-state storage or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The computing device 202 may include one or more input/output devices 208 such as a keyboard, a pointing device, a touchscreen, a microphone, a camera, a display, a speaker, a printer, and the like. Input/output devices 208 that are physically remote from the processing unit(s) 204 and the computer-readable media 206 (e.g., the monitor and keyboard of a thin client) are also included within the scope of the input/output devices 208.

A network interface 210 may also be included in the computing device 202. The network interface 210 is a point of interconnection between the computing device 202 and a network 212. The network interface 210 may be implemented in hardware for example as a network interface card (NIC), a network adapter, a LAN adapter or physical network interface. The network interface 210 can be implemented in part in software. The network interface 210 may be implemented as an expansion card or as part of a motherboard. The network interface 210 implements electronic circuitry to communicate using a specific physical layer and data link layer standard such as Ethernet, Infini-Band, or Wi-Fi. The network interface 210 may support wired and/or wireless communication. The network interface 210 provides a base for a full network protocol stack, allowing communication among groups of computers on the same local area network (LAN) and large-scale network communications through routable protocols, such as Internet Protocol (IP).

The network 212 may be implemented as any type of communications network such as a local area network, a wide area network, a mesh network, an ad hoc network, a peer-to-peer network, the Internet, a cable network, a telephone network, and the like.

A device interface 214 may be part of the computing device 202 that provides hardware to establish communicative connections to other devices such as the polynucleotide sequencer 120, etc. The device interface 214 may also include software that supports the hardware. The device interface 214 may be implemented as a wired or wireless connection which does not cross a network. A wired connection may include one or more wires or cables physically connecting the computing device 202 to another device. The wired connection may be created by a headphone cable, a telephone cable, a SCSI cable, a USB cable, an Ethernet cable, or the like. The wireless connection may be created by radio waves (e.g., any version of Bluetooth, ANT, Wi-Fi IEEE 802.11, etc.), infrared light, or the like. For example, the reads 122 may be received by the computing device 202 from the polynucleotide sequencer 120 via the device interface 214. In some implementations, for example if the polynucleotide sequencer 120 is located remote from the computing device 202, the reads 122 may be transmitted to the computing device 202 via the network 212 and the network interface 210.

The computing device 202 includes multiple modules that may be implemented as instructions stored in the computer-readable media 206 for execution by processing unit(s) 204 and/or implemented, in whole or in part, by one or more hardware logic components or firmware.

The payload extraction module 124 performs clustering of reads 122 as described above. The payload extraction module 124 may receive data including the reads 122 as one or more files from the polynucleotide sequencer 120. Those files may contain additional information beyond the nucleotide sequence such as quality scores. However, the payload extraction module 124 may disregard the quality scores or other metadata and act only on the strings of sequence data (e.g., strings of A's, G's, C's, T's) received from the polynucleotide sequencer 120. The payload extraction module 124 may include one or more additional modules such as a hashing module 216, and edit distance module 218, an exact match module 220, and a primer location prediction module 222.

The payload extraction module 124 may also be provided with the sequences of forward primers and reverse primers used to amplify the polynucleotide molecules 110. Identity of the primers is known because these are the same primers that were used in any PCR reaction to amplify the polynucleotide molecules 110 prior to sequencing. If the polynucleotide sequencer 120 is provided with multiple different PCR products, then the payload extraction module 124 may be provided with the sequences of multiple different pairs of forward primers and reverse primers. Primer sequences, the subsequences that are present in the reads 122, are the reverse complement of the primer sequences. Thus, the payload extraction module 124 may be provided with multiple subsequences of approximately 18 to 22 characters of A's, G's, C's, and T's that represent the primer sequences. Primer sequences can refer to the sequence of the primers themselves, the sequence of a region of a polynucleotide to which the primer binds, or a sequence of a complementary strand of a polynucleotide that hybridizes to the region where a primer can bind. The paired relationships between a forward primer and a reverse primer may also be provided to the payload extraction module 124. For example, forward primer A may be identified as being paired with reverse primer A', forward primer B is noted as being paired with reverse primer B', etc. Correlation between a primer or pair of primers and an original data source such as a computer file may also be provided to the payload extraction module 124. This correlation may indicate that any payload 114 adjacent to forward primer D contains information associated with the computer file 123.MP3. A list of primer sequences and/or a list of associations between primers and specific computer files may be stored in the computer-readable media 206.

The hashing module 216 calculates hashes for the reads 122 and primer sequences. A hash function h(x) is any function that can be used to map data of arbitrary size to data of fixed size. The values returned by a hash function are called hash values, hash codes, digests, or simply hashes. Hashes are used by the hashing module 216 to find an approximate location of primer sequences in the reads 122 based on similarities between hashes. The degree of similarity between hashes may be referred to as distance. Similar hashes are only a small distance from each other while vastly different hashes are a large distance apart.

The hashing module 216 may be searching for locations in millions of reads 122 that contain a subsequence which matches any one of thousands of different primer sequences. The primer site binding sequences and the sequences of the reads 122 may be referred to as strings. A string is simply a sequence of characters (e.g., ACTTACG).

The hashing module 216 is not limited to using a single specific hash function but can use any hash function h(x) that has three characteristics:

If the edit distance between two strings x and y of length L is small, then the distance between the hashes of those strings, h(x) and h(y), is also small.

If the edit distance between two strings x and y is large, then there is a high probability that the distance between hashes of those strings, h(x) and h(y), is also large.

Given the hash value h(a#x), computing the value of h(x#b) can be done quickly, where x is a string, a and b are two arbitrary character; a#x and x#b are concatenations of a and x, and x and b respectively. Furthermore, given the distance between h(a#x) and h(y), the distance between h(x#b) and h(y) can be found quickly.

The first two characteristics specify that the hash function h(x) approximates edit distance in terms of finding the similarity between a primer sequence and a subsequence of a read 122. The third characteristic indicates that shift in the location of a subsequence by one base pair results in only a small change in the value of the hash and in the distance from the hash of a primer binding site.

One technique, but not the only technique, for creating hashes with the above characteristics is k-mer embedding. The term k-mer typically refers to all the possible substrings of length k that are contained in a string. k is an integer such as 1, 2, 3, 4, 5, etc. In the analysis of polynucleotides, k-mers may refer to all the possible subsequences (of length k) from a read 122. The number of k-mers possible given a string of length L is, L−k+1. Thus, if the length L for a primer equals 20 and the length k of the k-mers is 3 (i.e., trimers), then there are 18 trimers. The number of possible k-mers sequences given n possibilities for each position in the k-mers (4 in the case of polynucleotides with natural bases e.g. ACTG) is $n^k$. Continuing with the previous example, if there are four possible nucleotides for each position, n=4, and the k-mers are trimers, there are 64 different three-base combinations that could be a k-mer in the primer binding site.

The hashing module 216 uses k-mers for efficient approximate matching. By converting the sequences of the primer binding sites and of the reads 122 into sets of k-mers, it is possible to embed the resulting k-mers in a vector space thus allowing for efficient comparison of similarities. Thus, the hash function h(x) may be a vector in $4^k$ dimensional space $\mathbb{Z}^{4^k}$. If k=3 (trimers) then the vector space has 64 dimensions. The coordinates of this space are indexed by k-mers i.e. strings of length k in the alphabet {A, C, G, T}. The t-th coordinate of h(x) equals the number of occurrences of t in x. Thus, the possible trimers given the alphabet {A, C, G, T} are {AAA, AAG, AAC, AAT, AGA, AGG, AGC, AGT, ACA, ACG, ACC, ACT, ATA, ATG, ATC, ATT, GAA, GAG, GAC, GAT, GGA, GGC, GGG, GGT, GCA, GCG, GCC, GCT, GTA, GTG, GTC, GTT, CAA, CAG, CAC, CAT, CGA, CGG, CGC, CGT, CCA, CCG, CCC, CCT, CTA, CTG, CTC, CTT, TAA, TAG, TAC, TAT, TGA, TGG, TGC, TGT, TCA, TCG, TCC, TCT, TTA, TTG, TTC, TTT}. The 1st coordinate of h(x) may be the number of time AAA is present in a string (e.g., 0, 1, 2, etc.). Therefore, hashes will be a series of 64 integers with most being zero. Non-zero values will be present only when the corresponding k-mer is found in the base string. Assuming a roughly random distribution of nucleotide bases throughout the reads 122 and the primers, a length L of 20, and use of trimers, most k-mers present in a string will occur only once and a much smaller number will be present two or more times.

The length of the strings should be less than $4^k$. If the length of a string is longer, the probability of the string containing all or almost all possible k-mers increases. Because the length of primers is typically around 20 bp the string length will be about the same. For example, if k=1 then $4^k$ is much less than 20 and most hashes would be a string of 1's making it difficult to differentiate between two strings by using the hashes. If, as in the example above, k=3 then $4^k$ is 64 which is longer than 20 making trimers a suitable choice given typical primer lengths.

There are multiple ways the hashing module 216 can calculate a distance between two hashes h(x) and h(y). The first string hashed may be a substring x of a read 122. The second string hashed may be a primer sequence y. The substring x may have the same length as string y. For example, the primer sequence y may have a length of 20 and the substring x will also have length 20. Comparing two hashes created according to the k-mer embedding technique describe above comprises comparing two 64-digit strings of integers.

One way to measure distance between two hashes is $L_1$ distance. $L_1$ distance may also be known as taxicab metric, rectilinear distance, $l_1$ norm, snake distance, city block distance, Manhattan distance, or Manhattan length. The $L_1$ distance, $d_1$, between two vectors such as the hashes h(x) and h(y) is an n-dimensional real vector space (e.g., 64-dimensional) with fixed Cartesian coordinate system, is the sum of the lengths of the projections of the line segment between the points onto the coordinate axes. This is represented formally as follows:

$$d_1(h(x), h(y)) = \|h(x) - h(y)\|_1 = \sum_t |h_t(x) - h_t(y)|$$

An alternative to $L_1$ distance is Hamming distance. The Hamming distance, $d_H$, between two strings of equal length is the number of positions at which the corresponding symbols are different. In other words, Hamming distance measures the minimum number of substitutions required to change one string into the other, or the minimum number of errors that could have transformed one string into the other. If, as in the example above, the hash function uses k-mer embedding, then the Hamming distance is the number of k-mers where
the counts are different. Hamming distance may be calculated as follows:

$$d_H(h(x), h(y)) = \sum_t 1(h_t(x) \neq h_t(y))$$

A third technique for calculating distances between two hashes is by counting the number of positions that are zero in one of the hashes but non-zero in the second hash. Recall that for many hashing techniques, such as k-mer embedding, the hashes will likely include many positions that are zero, some that are one, and many fewer that are two or greater. Considering only zero/non-zero differences does not distinguish between k-mers that are present once or more than once in a string. However, this is sufficient for finding the approximate position of a primer sequence. Formally, the distance based on non-zero positions, $d_{\neq 0}$, is represented as follows:

$$d_{\neq 0}(h(x), h(y)) = \sum_t |1(h_t(x) \neq 0) - 1(h_t(y) \neq 0)|$$

All of the three techniques described above have the three characteristics specified for the hash function h(x). However, suitable techniques for calculating distances between hashes or vectors are not limited to the examples provided above.

The hashing module 216 may calculate distances between all known primer sequences and multiple subsequences of the reads 122. This will be a very large number of comparisons for a typical data set thus computational efficiency is important. Calculating edit distances for each of these comparisons would take significantly more time because the running time for edit distance calculations is quadratic while the running time for creations of hashes and calculating hash distances is linear.

The distance between two hashes (e.g., $d_1$, $d_H$, $d_{\neq 0}$, or another metric) may be compared to a threshold distance T by the hashing module 216. A threshold difference is set as a particular threshold distance to balance between limiting false positives while still detecting true matches. A false positive mistakenly indicates that the hash of a subsequence of a read 122 matches the hash of a primer sequence. A false negative, failing to detect a match, mistakenly indicates that the hash of a primer sequence is not similar to the hash of a subsequence of a read 122 that does have a sequence which is similar to the primer sequence. The specific value for the threshold distance may depend on the technique used for calculating distance. The threshold value may be set manually by a user, for example, based on prior experience or results. In an implementation, the threshold may be set so that on average two primer sequences are found in each read 122. Pairs of hashes with distances less than the threshold may be passed to the edit distance module 218 for further analysis.

The edit distance module 218 calculates edit distances between two strings such as a primer sequence and a subsequence of a read 122. The edit distance module 218 compares actual nucleotide bases values (e.g., A, C, G, and T) not hashes. An "edit distance" is equal to the minimum number of insertions, deletions, and substitutions required to transform one sequence into another sequence. For example, given a first polynucleotide sequence, X, is ACGTTAC and a second polynucleotide sequence, Y, is CGTCTAG, the edit distance between X and Y, ed(X, Y), is 3. An, illustrative conversion showing the three steps is below.

```
ACGTTAC → CGTTAC (delete first A)

CGTTAC → CGTATAC (add A between the T's)

CGTATAC → CGTATAG (substitute G for the final C)
```

Techniques for determining edit distance include the Wagner-Fischer algorithm which is a dynamic programming algorithm that computes the edit distance between two strings. The Wagner-Fischer algorithm computes edit distance based on the observation that if a matrix is reserved to hold the edit distances between all prefixes of the first string and all prefixes of the second string, then the values in the matrix can be computed by flood filling the matrix, and thus finding the distance between the two full strings as the last value computed. Another edit distance algorithm is Hirschberg's algorithm which is also a dynamic programming algorithm that finds the optimal sequence alignment between two strings. Optimality is measured with the Levenshtein distance. The Levenshtein distance is a string metric for measuring the difference between two strings and is defined to be the sum of the costs of insertions, replacements, deletions, and null actions needed to change one string into the other. The costs may be the same for all types of changes or weighted differently. For example, the cost of insertions and deletions may be higher than the cost for replacements.

The edit distance between two sequences of length L can be computed in quadratic time $O(L^2)$ using a dynamic programming algorithm such as the Wagner-Fischer algorithm or Hirschberg's algorithm. Dynamic programming refers to solving a complex problem by breaking it down into a collection of simpler sub-problems, solving each of those sub-problems just once, and storing their solutions. The next time the same sub-problem occurs, instead of recomputing the solution, the previously computed solution is retrieved from memory such as from the computer-readable media 206, thereby saving computation time at the expense of a modest expenditure in storage space. Each of the subproblem solutions is indexed in some way, typically based on the values of its input parameters, so as to facilitate lookup. The technique of storing solutions to subproblems instead of recomputing them can be referred to as "memoization."

Due to the quadratic time complexity of calculating edit distances, limiting the portions of the reads 122 over which edit distance is calculated can reduce computational expense. The edit distance module 218 may do this by identifying an evaluation window in a read 122 based on the matches found by the hashing module 216. Because the hashing module 216 identifies approximate matches based on comparison of hash values, it is possible that the actual match between a primer sequence and a subsequence of a read 122 is in a slightly different location than the location identified by the hashing module 216. Thus, the evaluation window may include the subsequence of the read 122 identified by the hashing module 216 and additional bases from the read 122. Evaluation windows are described in greater detail below in the description of FIG. 5.

The edit distance module 218 calculates edit distances between subsequences in the edit distance window and one or more primer sequences in order to determine a best-match subsequence within the evaluation window that has a smallest edit distance from the primer sequence relative to other subsequences within the evaluation window. The best-match subsequence is the subsequence in the read 122 that "matches" the primer sequence accounting for any errors present in the sequence of the read 122. Thus, the best-match subsequence may, but does not necessarily, have the same length as the primer sequence. In an implementation, the edit distance module 218 may use dynamic programming to identify the best-match sub-sequence by recursively calculating edit distances for subsequences the same length as the primer sequence within the evaluation window by advancing the region of comparison one base pair per iteration.

The edit distances may be compared to a threshold distance. For example, the threshold distance may be one, two, three, or another value. As the edit distance between a primer sequence and a subsequence in the evaluation window are being compared by the edit distance module 218, if the distance exceeds the threshold difference, then the edit distance module 218 may abandon the calculation before evaluating the entire length of the subsequence because further evaluation will not decrease the edit distance. Abandoning edit distance calculations before completion in this way can provide additional computational efficiency. The threshold may be set by a user based on experience or results from previous use of this technique. It is possible that every subsequence within an evaluation window may be more than the threshold distance from the primer sequence. This may indicate that the approximate location found by the hashing module 216 is incorrect.

Although many reads 122 may have errors in the subsequences corresponding to primer sequences, there may be some that match exactly. Exact matches can be identified by the exact match module 220. Identifying exact matches is computationally less expensive than identifying approximate matches and finding locations in the reads 122 which exactly match one of the primer sequences can reduce later analysis and associated computational expense. Thus, in some implementations the exact match module 220 may process the primer sequences and the reads 122 prior to the hashing module 216 and/or the edit distance module 218. The exact match module 220 may use any suitable technique for finding an exact match between two strings.

For example, the exact match module 220 may determine if the sequence of a primer P is a subsequence of a read 122. Finding subsequences that match exactly can be done quickly by using an edit distance algorithm to identify locations where the edit distance is zero.

Another technique for identifying exact matches is to build a deterministic finite automaton (DFA) Q that given a subsequence s checks whether s contains one of the primer sequences $P_i$ as a substring. A DFA is a finite-state machine that accepts and rejects strings of symbols and only produces a unique computation (or run) of the automaton for each input string which in this application is one of the reads 122. A separate DFA can be built for each one of the reads 122. A DFA can be thought of as a collection of states. The number of states is based on the number of primer sequences that are built into the DFA. For the examples used in this disclosure, the DFA may have approximately 1000 states. The running time of the automaton Q is linear in the length of s and does not change substantially as the number of primers increases (i.e., the size of Q grows linearly with the number of primers $P_i$). Thus, in one pass over s, the automaton Q can find all exact matches of primers $P_i$ in s.

Deterministic in DFA refers to the uniqueness of the computation. The DFA takes a finite sequence of nucleotide base values (e.g., A, G, C, and T) as input. For each state, the number of possible transitions is the same as the number of unique nucleotide bases (e.g., four if only the natural bases are used). Upon reading a base value, the DFA jumps deterministically from one state to another state representing a subsequent base value in the read 122. A DFA has a start state before any base values have been read where computations begin, and a set of accept states (or special states or terminal states) which define when a sequence matches a known primer sequence. Due to the DFA entering an accept state only when the read matches the primer sequence exactly, DFAs do not typically identify approximate matches. These special states are associated with identifiers that indicate a particular primer (e.g., special states 1-50 where each state is correlated with a primer sequence). Thus, one DFA may be built that represents all of the primer sequences. DFAs are a practical model of computation because there is a trivial linear time, constant-space, online algorithm to simulate a DFA on a stream of input.

In one implementation, the DFA states are all possible prefixes of primers of all lengths. When scanning a read 122, the DFA is traversed and on each step the state corresponds to the longest primer prefix that ends at the current position in the read 122. DFA states that correspond to complete primers (trivial prefixes) are special, as they correspond to exact matches.

Thus, the exact match module 220 can function to identify an exact match between a primer sequence and sub-sequences of a read by determining that the sub-sequence of the read has an edit distance of zero from the primer sequence, by building a deterministic finite automaton (DFA) having an accept state representing the primer sequence, or by any other suitable technique.

Any subsequences of the reads 122 that are identified as an exact match for one of the primer sequences may be excluded from evaluation by the hashing module 216 and/or the edit distance module 218 thereby reducing the amount of sequences within the reads 122 that are analyzed using the more computationally expensive processes. However, in some implementations in which there is known to be a large number of errors or high noise in the reads 122, exact matching may be omitted due to the low likelihood of finding any subsequences in the reads 122 that match exactly a primer sequence. One example of this is reads 122 from Nanopore sequencing technology because these reads may have greater than 10% error rates making unlikely that there will be any exact matches.

The primer location prediction module 222 may predict locations in the reads 122 where a primer sequence is likely to be located. The specific locations may then be evaluated by the edit distance module 218 to determine if there is a primer sequence. Any suitable heuristic may be used by the primer location prediction module 222 to identify a location where a primer sequence is likely found. Such heuristics are ways to focus the use of the edit distance module 218 thereby reducing the number of computationally expensive edit distance calculations. The primer location prediction module 222 may also be used to guide initial comparisons by the exact match module 220.

In an implementation, a known length of a payload 114 and a location of a first primer sequence may be used to identify a likely location for a second primer sequence. Because the sequences of the polynucleotide molecules 110 are intentionally designed, the length of the payload 114 is known and the positioning of the payload 114 relative to the primer binding sites 116 is also known. For example, the length of the payload 114 may be 130 bp. Thus, if a primer sequence is identified in a read 122, it is likely that another primer sequence will be begin 131 bp away. Edit distance calculations to identify the second primer sequence may be limited to evaluating only a known sequence of a paired primer sequence that is paired with the primer sequence already identified. Thus, if the primer sequence corresponding to a known forward primer is located, then the primer sequence for the paired reverse primer will be compared to the sequence of the read 122. Of course, errors in the reads 122 such as additions deletions, and concatenations of sequences from separate polynucleotide molecules 110 will result in some instances where the distance between two primer sequences sites is not the same as the known length of the payloads 114. The hashing module 216 can operate independently from the primer location prediction module 222 and identify possible locations for primer sequences without use of prediction heuristics.

In an implementation, the primer location prediction module 222 may use an offset from the start or end of a read 122 to identify the location where primer sequence is likely. This offset may be based on the type of sequencing technology used by the polynucleotide sequencer 120. Some sequencing technology (e.g., sequencing-by-synthesis) may add additional bases to the polynucleotide molecules 110 to facilitate sequencing. These additional bases may appear at the ends of a read 122 and the number of additional bases may be constant or roughly the same across all reads 122. The offset length may be identified based on experience and past results. For example, primer sequences may frequently be found five base pairs from the beginning of a read 122. Thus, the primer location prediction module 222 may evaluate a subsequence of the read 122 starting on the sixth base pair to determine if the edit distance of that subsequence is close to any of the primer sequences. This prediction may identify a single subsequence of the read 122 for evaluation by the edit distance module 218 without use of the hashing module 216.

Thus, the primer location prediction module 222 identifies subsequences in the reads 122 to search first. Depending on the number of primer sequences found, the length of the reads 122, the sequencing technology, and the design of the polynucleotide molecules 110, use of the primer location prediction module 222 may reduce the number of operations performed by the hashing module 216 and/or the edit distance module 218. Limiting application of edit distance comparisons to only regions where primer sequences are likely may also serve to reduce the detection of false positives. False positives may be particularly likely in reads 122 with high error rates (e.g., Nanopore reads) because the high rate of error may alter a subsequence in the payload region enough so that it is similar to a primer sequence. Heuristics provided by the primer location prediction module 222 may also be useful for analyzing reads 122 created by Nanopore sequencing because those reads may include forward and/or reverse primer sequences without the corresponding primer sequence for the paired primer.

The payload extraction module 124 may also include a payload grouping module 224. The payload grouping module 224 groups payload regions of the reads 122 that contain encodings of the same original binary data 104. The payload grouping module 224 may operate by identifying as a payload region any subsequence in a read 122 that is between two primer sequences. Rather than identifying any subsequence between two primer sequences as a payload region, the payload grouping module 224 may apply a more exacting criterion and only identify payload regions located between two primer sequences that corresponds to a paired set of forward and reverse primers. Identification of the payload regions and of respective payload regions' associations with primer sequences, enables the payload grouping module 224 to extract only payload regions and group payload regions that contain portions of the same set of data. The grouping may be implemented by clustering payload sequences based on associated primer sequences, attaching metadata to payload sequences, or by any other technique.

In some implementations, the reads 122 output from the polynucleotide sequencer 120 may already be clustered prior to any operations of the payload extraction module 124. For example, if the polynucleotide molecules 110 sequenced by the polynucleotide sequencer 120 were all amplified using the same single pair of primers and that pair of primers is exclusively associated with the computer file 102, then all of the reads 122 will contain payload sequences that encode portions of the same source data. However, even in this situation operations of the payload extraction module 124 are useful for processing the raw data output by the polynucleotide sequencer 120 into a format that is amenable for decoding into a decoded computer file 128 or other decoded data. Specifically, even when a set of reads 122 is already clustered, identification of the exact locations of the primer sequences may be used to identify the payload regions of the reads 122. The payload regions can then be extracted from other portions of the reads 122 for further processing in order to decode the information stored in the payload regions. Aspects of the decoding processes may be highly sensitive to changes in the sequence of the payload region, so identifying the correct starting position of the payload regions may be valuable even for a set of reads 122 that all contain data from the same original source.

Figure 3:
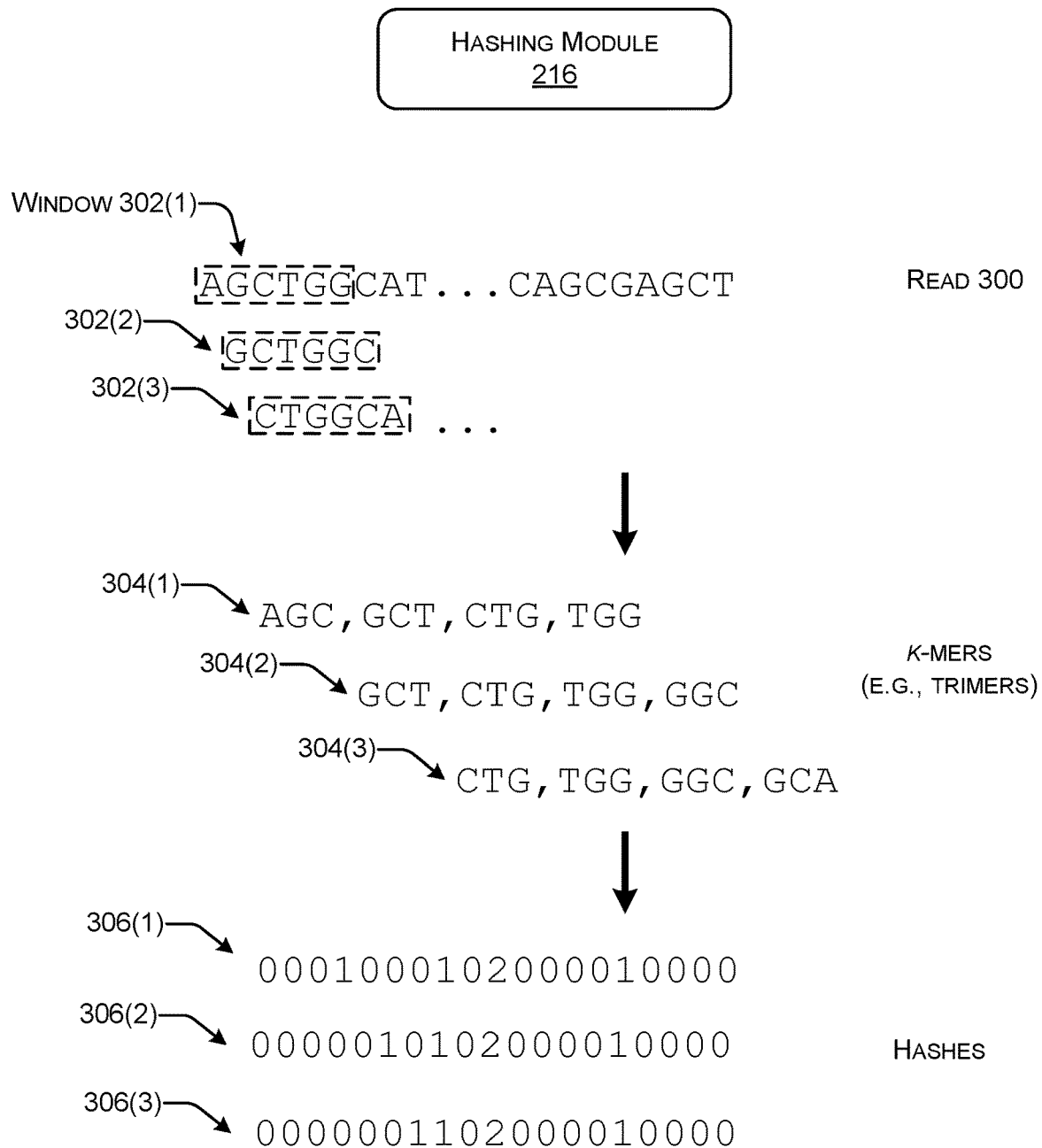
FIG. 3 shows a technique for creating hashes of polynucleotide reads.

FIG. 3 shows further details regarding an illustrative technique that may be used by the hashing module 216 to create hashes. The read 300 represents sequence data coming from a polynucleotide sequencer. For example, the read 300 may be the same as one of the reads 122 introduced in FIG. 1. This read 300 may be hashed using a rolling hash. A rolling hash (also known as recursive hashing or rolling checksum) is a hash function where the input is hashed in a window 302 that moves through the input. The length of the window 302 may be the same as the length of a primer (and thus the same as the length of a reverse complementary primer binding site).

For example, the read 300 may have a length of 200 bp which is longer than the typical 20-bp length of a primer. Thus, the hash function h(x) may be applied iteratively to some or all of the subsequences in the read 300 that are 20 bp long. Application of a rolling hash is illustrated in FIG. 3 as a 6-bp long window 302 moving from left to right along read 300. The window 302 may also move from right to left. The hash of the sequence in the window 302(1) at the start of the read 300 may be calculated anew based on h(x). After advancing one bp along the read 300, the window 302(2) contains a different series of nucleotide values. However, because the window 302 has shifted one bp along read 300, the change between the nucleotides in the window 302(1) at its starting position and the window 302(2) after the first shift is only the omission of the initial A and addition of a C. A further single-bp shift moves the window 302(3) farther along the read 300 and the sequence of nucleotides in the window 302(3) changes relative to the previous window 302(2) position by addition of one nucleotide and loss of one nucleotide. Thus, any two adjacent window 302 positions contain most of the same nucleotide values.

This process of "rolling" the window 302 along the read 300 allows the value of h(x) to be updated rather than calculated anew due to the characteristic of h(x) that given the hash value h(a#x) (e.g. h(AGCTGG), calculating the value of h(x#b) (e.g., h(GCTTGC) can be much faster than calculating an entirely new hash value. After a hash is computed for the first subsequence of the read 300, hashes of other subsequences may be computed by dynamically updating h(x) based on the one-bp shift in the portion of the read 300 being hashed. Use of a rolling hash to create a number of hashes from different subsequences or windows within the read 300 is not limited to any particular hash function.

As discussed above, one technique for creating a hash from a nucleotide sequence is to create a vector based on k-mer embedding. By converting the subsequences of the read 300 into sets of k-mers, it is possible to embed the resulting k-mers in a vector space thus allowing for efficient comparison of similarities. Thus, the hash function h(x) may be a vector in $4^k$ dimensional space $\mathbb{Z}^{4^k}$. If k=3 (trimers) then the vector space has 64 dimensions. In FIG. 3, k=3 and sets of trimers are identified in the windows 302(1), 302(2), 302(3). Each shift of the window 302 along the read 300 results in a different set of k-mers 304. The set of k-mers 304(1) corresponding to the subsequence included in the first window 302(1) from the read 300 in this example are ACG, GCT, CTG, and TGG. The sets of k-mers 304(2), 304(3) from subsequent windows 302(2), 302(3) of the read 300 vary by the addition of one k-mer and the removal of one k-mer relative to the adjacent window 302. For example, the set of k-mers 304(2) corresponding to the second window 302(2) loses the AGC timer and gains a GGC trimer relative to the first window 302(1). Thus, updating h(x) for each shift in the window 302 changes only two k-mers. Dynamic programming may be used with this technique by storing the previous k-mer values and recalling the stored values from memory so that the only new calculation is for the one new k-mer (e.g., GGC).

Hashes 306 may be created from the k-mers as described previously by mapping to a vector space that has a dimension for each of the possible k-mers. The count of each k-mer can be the value of the vector in that dimension. Thus, if the timer AGC was present in a window 302 two times, the value for that part of the vector would be 2. Use of k-mer embedding as the hashing technique generates hashes 306(1), 306(2), 306(3) that are strings of integers with mostly 0's, some 1's, and a few higher numbers. Due to the similarity in trimers between adjacent windows 302, the values of the corresponding hashes will also be similar.

Figure 4:
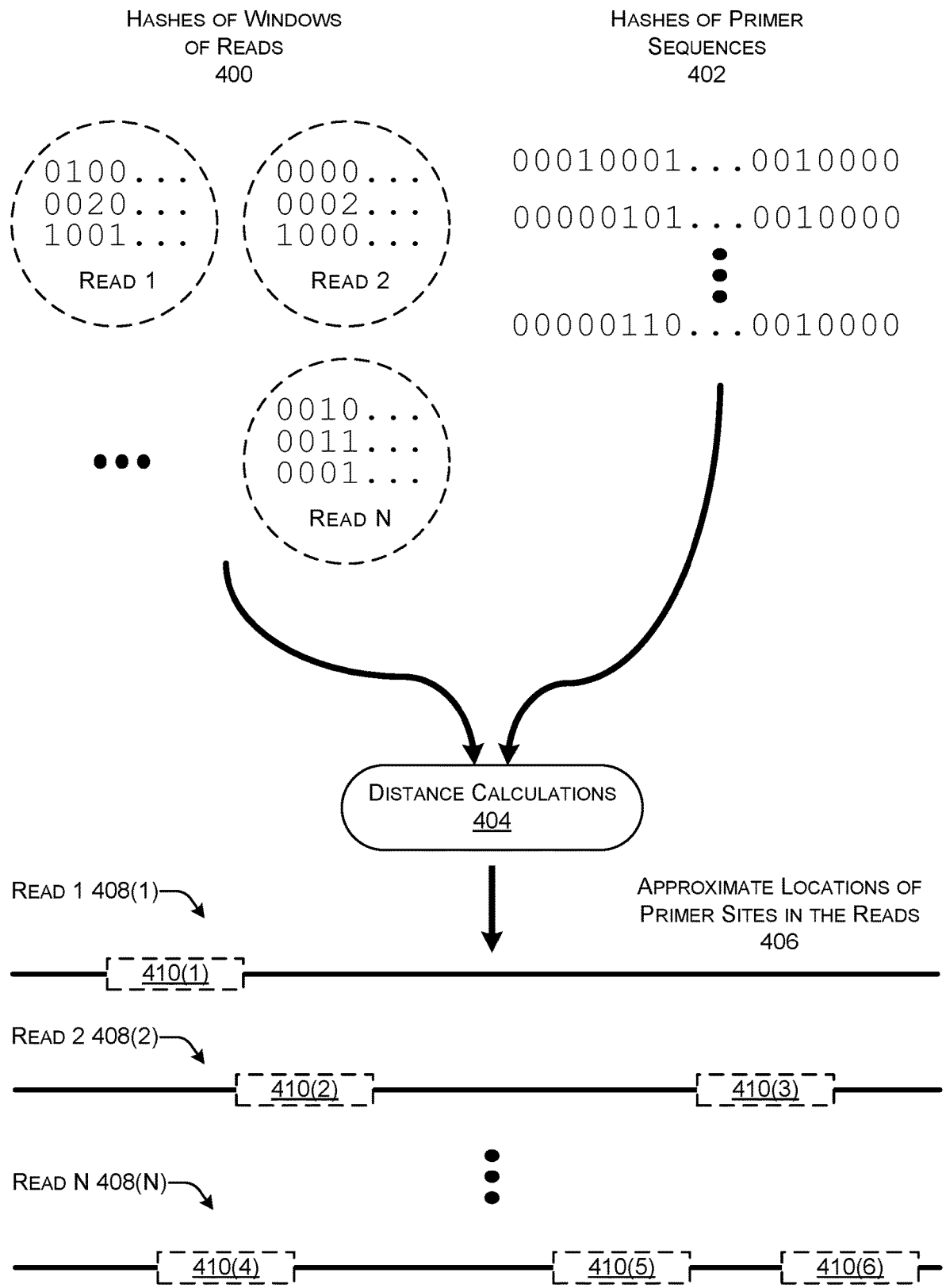
FIG. 4 shows a technique for finding approximate locations of primer sequences based on hashes.

FIG. 4 shows further details regarding an illustrative technique for the hashing module 216 to find approximate locations of primer sequences. Creating a hash of a read, such as the read 300 as shown in FIG. 3, results in a collection of multiple hashes 400 for the read. For example, if the length of the read is 200 base pairs, and the length of the window is 20 base pairs, then there may be 181 hashes generated from that single read. Each hash is associated with a particular subsequence of the read corresponding to the position of the window in the read used for generation of that hash.

Hashes of primer sequences 402, $h(P_i)$, may also be created by the hashing module 216. Hashes of the primer sequences 402, $h(x)$, are created in the same manner as the hashes of the subsequences of the reads. In an implementation, the primer sequences may be retrieved from the computer-readable media 206 and processed by the hashing module 216. Unlike the longer reads, a hash of a primer sequence may be represented as a fixed vector. In other words, the rolling hash technique is not applied to the primer sequences because those sequences are hashed in their entirety and not broken into shorter subsequences. Continuing with the example above, both the hashes of the windows of the reads 400 and the hashes of the primer sequences 402 may be 64-dimensional vectors. Distance calculations 404 are performed between one of the hashes of windows of the reads 400 of the hashes of the primer sequences 402. The distance calculations 404 may use any suitable technique for calculating distances between two vectors or hash values. For example, distances between hashes may be calculated by Hamming distance, $L_1$ distance, and the number of zero/non-zero differences at the same positions in two hashes. If the distance between $h(x)$ and $h(P_i)$ is small (e.g., less than a certain threshold) the subsequence of the read corresponding to x may be recorded as a match for the primer sequence $P_i$. The value of the threshold may be tuned by a user during searching and/or developed based on performance of past searches. In an implementation, instead of calculating distances for each subsequence of a read anew, the hash distance may be updated based on a distance previously calculated for a hash of a read subsequence that is shifted one nucleotide along the read. For example, the distance calculation for hash 306(2) in FIG. 3 may be determined by updating the distance of hash 306(1) based on differences between the already-evaluated hash 306(1) and the next hash 306(2).

The results of the distance calculations 404 are identification of approximate locations of primer sequences in the reads 406. In FIG. 4, a read 408 is illustrated as a solid line. A matching location 410 on a read 408 is represented as a dashed box. Each read 408 may have zero, one, two, or more matching locations 410. Read 1 408(1) has one matching location 410(1). A read 408 in which no matching locations 410 are identified, may be discarded and omitted from further analysis. It may be common for a single read 408 generated through sequencing-by-synthesis to have two matching locations 410. For example, read 2 408(2) has two matching locations 410(2) and 410(3). The longer reads generated by Nanopore sequencing may have sequences from multiple different polynucleotide molecules concatenated together resulting in reads with more than two matching locations 410. This technique can find all positions in one of the reads 408(1), 408(2), 408(N) that approximately match anyone of the primer sequences. In some implementations, however, only a portion of the hashes of the primer sequences 402 may be used for the distance calculations 404. For example, the distance calculations 404 may be limited to considering only hashes of primer sequences 402 corresponding to reverse primers. As additional example, if the primer sequence for a particular reverse primer has been located through exact matching, the distance calculations 404 may be performed only for the hash of a primer sequence corresponding to the forward primer paired with this reverse primer.

However, because the approximate match is a match between hashes not between actual polynucleotide sequences, edit distance may be used to confirm the approximate matches and precisely locate the subsequence of the read 408 that matches a one of the primer sequences.

Figure 5:
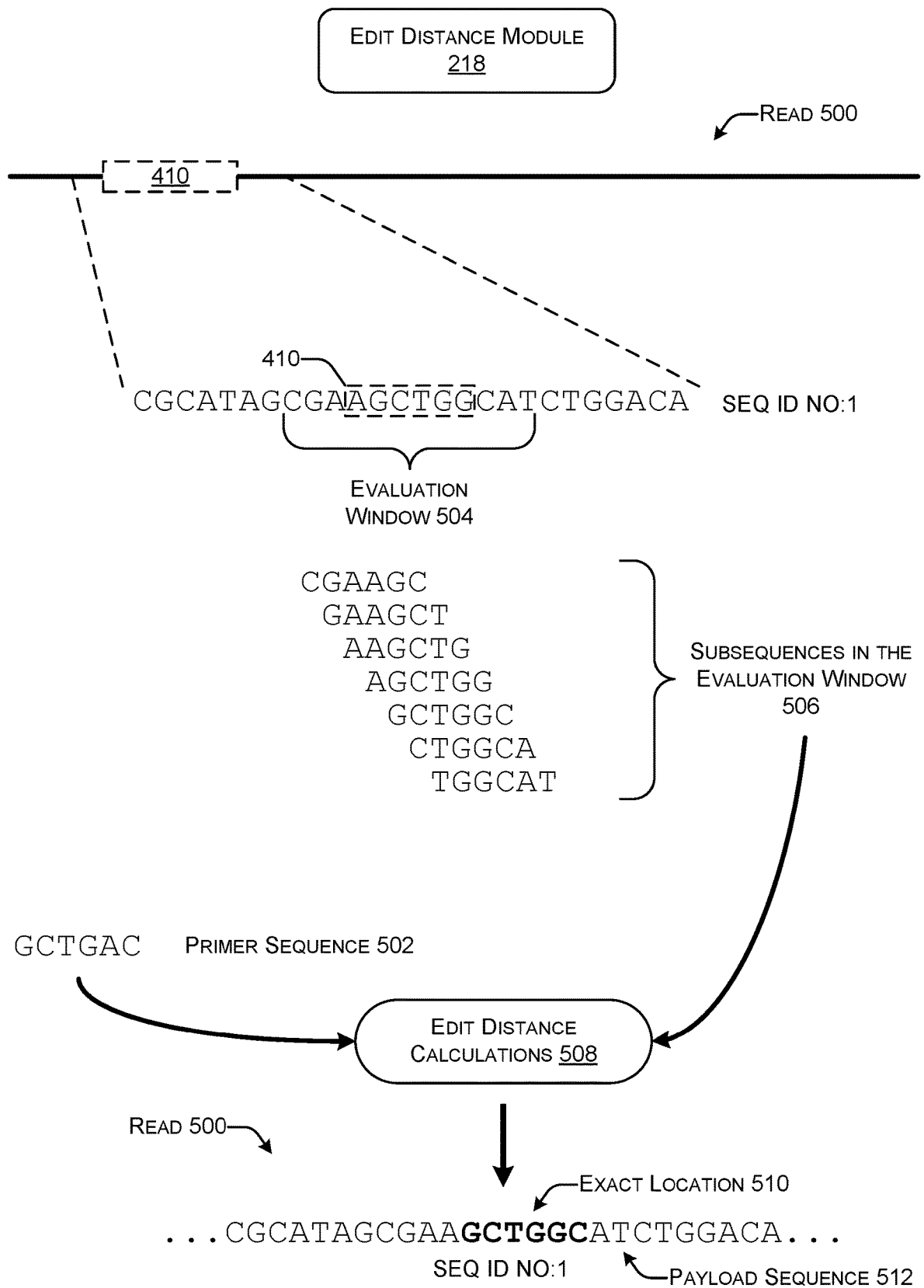
FIG. 5 shows a technique for calculating edit distance.

FIG. 5 shows further details regarding an illustrative technique performed by the edit distance module 218. As described previously, a read 500 may include one or more matching locations 410 identified based on comparison of hash values. In this example, the matching location 410 is six nucleotides long and includes the sequence AGCTGG.

Because, the comparison of hashes identifies an initial guess for the location of a primer sequence 502 only imperfectly, the subsequence of polynucleotides at the matching location 410 are approximate and may not have the smallest edit distance to the actual primer sequence 502. The best match for the primer sequence 502 along the read 500 may be shifted one, two, three, or more nucleotides away from the matching location 410. Thus, the edit distance module 218 may search for the best match for the primer sequence 502 along an evaluation window 504. The evaluation window 504 is longer than and also includes the matching location 410. For example, the evaluation window 504 may include 1, 3, 5, 10, etc. additional polynucleotide sequences on one or both sides of the matching location 410. The example illustrated in FIG. 5 shows three additional polynucleotide bases on each side of the matching location 410. As a further example, the evaluation window 504 may have a length that is a multiple of the primer length such as 1.1×, 1.2×, 1.5×, 2.0×, etc. Thus, the evaluation window 504 allows edit distances to be compared for a portion of the read 500 expanded beyond just the polynucleotide sequence that provided the matching location 410 but less than all of the read 500.

Each matching location 410 identified in a read 500 can be associated with its own evaluation window 504. Thus, if comparison of hash distances identifies three matching locations 410 in a read 500, then three separate evaluation windows 504 may be searched by the edit distance module 218. The matching location 410 is also associated with a particular primer sequence 502 because the matching location 410 is associated with a specific hash which in turn is associated with a primer sequence 502. Logically, the primer sequence 502 that was the basis for the match identified by comparing hash values is a reasonable choice for a comparison sequence to use in the edit distance calculations 508.

Within the evaluation window 504, there are multiple subsequences 506 that have the same length as the primer sequence 502. Thus, each one of the subsequences 506 may be compared to the primer sequence 502. Although this may involve making multiple edit distance calculations 508 (in this example as many as seven) this is fewer computationally expensive calculations than performing edit distance calculations 508 across the whole length of the read 500 for every one of the possible primer sequences. If, for example, a length of the read 500 is 200 bp, the number of primers is 100, the length of the primers is 20 bp, and edit distance was calculated between each primer sequence and every 20-bp long subsequence of the read 500, then (200−20+1)× 100=18,100 edit distance calculations would be necessary for each read 500. Restricting the portion of the read 500 over which edit distance is calculated and using a single primer sequence 502 in the edit distance calculations 508 both reduce the total number of computationally expensive edit distance calculations as compared to a naïve implementation.

The edit distance calculations 508 may compare a single primer sequence 502 to the subsequences 506 in the evaluation window 504 and identify an exact location 510 within the read 500 for the primer sequence 502. Specifically, the edit distance calculations 508 may find which subsequence 506 in the evaluation window 504 has a smallest edit distance to the particular primer sequence 502. Identifying a specific one of the subsequences 506 also locates the exact beginning and end of the primer sequence 502 in the read 500. Thus, the edit distance calculations 508 receives two strings A (i.e., primer sequence 502) and B (i.e., evaluation window 504) then finds a substring C (i.e., one of the subsequences 506) of B such that the edit distance between A and C is minimized and returns the edit distance between A and C along with the position of C. Substring C is thus identified as the primer sequence because its edit distance to the actual primer sequence is less than that of any other substring in the evaluation window. In this implementation, the edit distance calculations 508 do not compare A and B as is, but instead search for a substring C of B such that the distance between A and C is minimized.

This polynucleotide sequence at the exact location 510 does not necessarily have the same nucleotide sequence as the primer sequence 502 because of errors that may be present in the read 500. The sequence that is determined to be the exact location 510 may also have a different length than the primer because of additions or deletions. However, the exact location 510 represents the best match as determined by minimum edit distance for the primer sequence 502 within the evaluation window 504.

Identifying the position of the exact location 510 that is adjacent to the payload sequence 512 makes it possible to determine the starting position for the payload sequence 512. Finding the precise starting position (and ending position) for the payload sequence 512 can be important for later processing such as decoding the original data because a phase shift in the start of the payload sequence 514 by even one nucleotide position may result in the decoding process generating incorrect data. Finding the location of the payload sequence 512 may depend on the final (or the first) position of the exact location 510 and other features of the sequence at the exact location 510 may be less important. In the example in FIG. 5, the final C in the exact location 510 is used to identify the start of the payload sequence 512. If there was ambiguity regarding the other end of the sequence at the exact location 510 (e.g., uncertainty if the A just to the left of the sequence was included in the primer site or not), that type of ambiguity may be tolerated while still allowing for identification of the location of the payload sequence 512.

Calculating edit distances between the primer sequence 502 and the subsequences 506 from the evaluation window 504 may be made more efficient by comparing edit distances to a threshold and stopping a given edit distance calculations partway through if the value exceeds the threshold. Edit distances greater than the threshold distance may be categorized as not being a match between the primer sequence 502 and a one of the subsequences 506. The threshold may be manually set by a user or determined based on experience. In an implementation, the threshold may be the smallest edit distance found thus far in an evaluation window 504. Thus, if the edit distance for one subsequence 506 is two, then two will be set as the threshold and any other subsequence 506 with a larger edit distance will be identified as not being the best match.

For a given subsequence 506, edit distance calculations 508 may be performed iteratively character by character. An edit distance may be calculated for each character in the subsequence 506 with respect to the corresponding character in the primer sequence 502. If the characters are the same (e.g., both G) then the edit distance is zero. If all characters match, then the total edit distance is zero and the subsequence 506 is an exact match for the primer sequence 502. As the edit distance calculation 508 proceeds iteratively, each mismatch will increase the total edit distance. If the total edit distance exceeds the threshold distance, edit distance calculations 508 for that subsequence 506 may stop. This avoids unnecessary calculations to fully compare the subsequence 506 to the primer sequence 502.

If there is no subsequence 506 within the evaluation window 504 that has an edit distance less than the threshold distance from the primer sequence 502, the edit distance module 218 may determine that there is no match within the evaluation window 504. This may occur if the hashing module 216 identifies a false positive which is possible given the approximate nature of the hashes. In implementation is that do not use a threshold distance, the subsequence 506 with the smallest edit distance will be used to identify the exact location 510 in the read 500.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Figure 6:
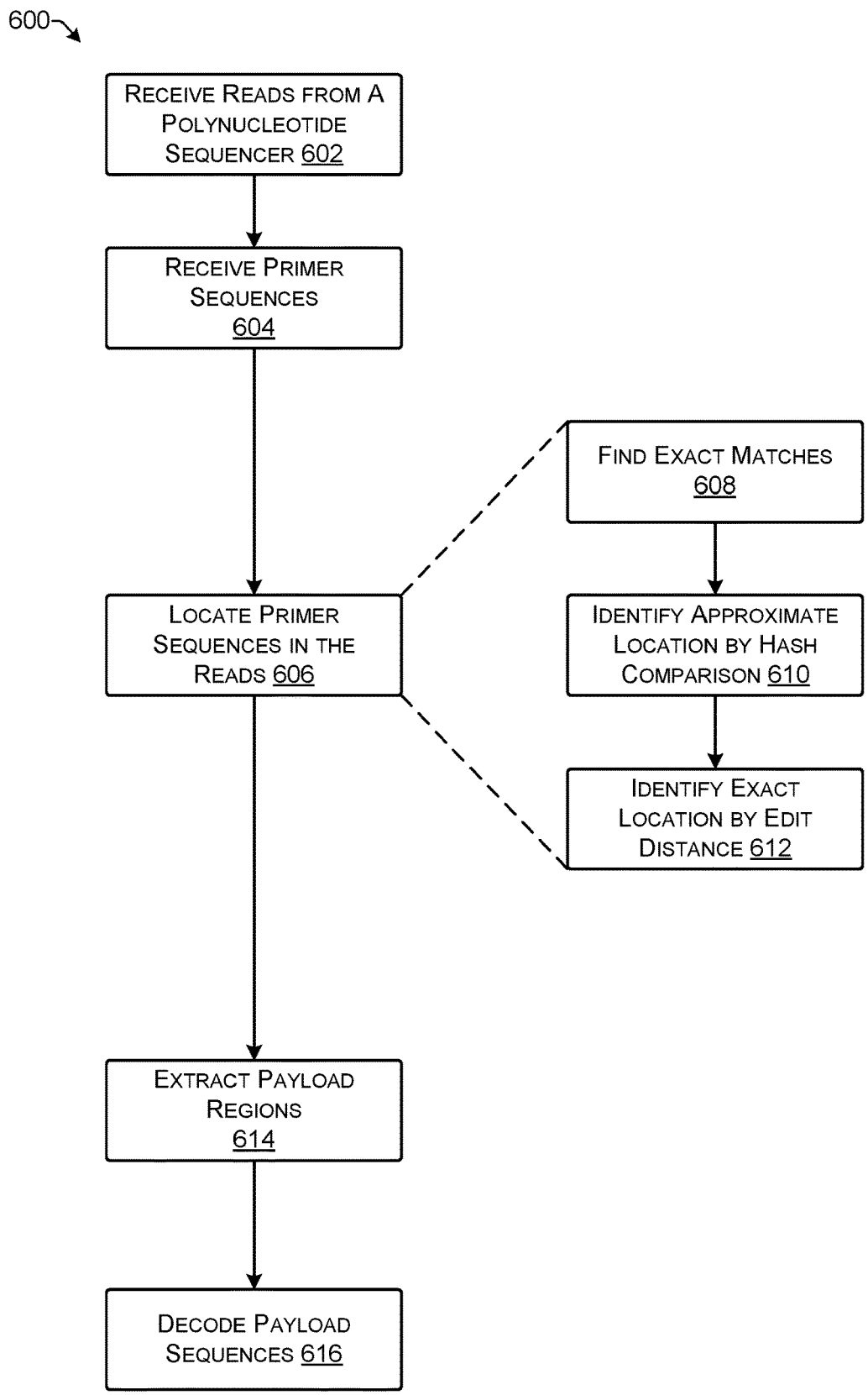
FIG. 6 illustrates a flow diagram of a technique for locating primer sequences and clustering payload regions.

FIG. 6 shows process 600 for locating primer sequences and extracting payload regions. The process 600 may be implemented in whole or part by the computing device 202 shown in FIG. 2.

At 602, a plurality of reads is received from a polynucleotide sequencer. The polynucleotide sequencer may be the polynucleotide sequencer 120 and the plurality of reads may be the same as the plural reads 122 shown in FIG. 1. In an implementation, the plurality of reads may be received by the computing device 202 via the device interface 214. Current sequencing technology may produce a very large number (i.e., 1,000,000,000 or more) of reads from a large number (i.e., 1,000,000 or more) of DNA strands.

At 604, a plurality of primer sequences are received. The primer sequences may be known based on the design of the polynucleotide molecules that were sequenced to generate the reads. The primer sequences may be stored, for example, in the computer-readable media 206 of the computing device 202 and received from storage by the payload extraction module 124.

At 606, primer sequences are located within the plurality of reads. The primer sequences in the reads also includes reverse complementary sequences that represent a binding site corresponding to one of the primer sequences. Locating primer sequences may include finding exact matches, identifying approximate locations by comparison of hash functions, and/or identifying exact locations in the reads by use of edit distance calculations. The primer sequences may be located by the payload extraction module 124.

At 608, exact matches between subsequences of the reads and the primer sequences are found. The exact matches may be identified by any suitable technique for finding an exact match between two sequences of nucleotides. For example, exact matches may be found by identifying subsequences of the reads that have edit distance of zero from one of the primer sequences. The zero edit distance indicates that there is an exact match. As a further example, exact matches may be found by building a deterministic finite automaton (DFA) having except states representing the primer sequences. Thus, if an except state is reached during a run of the DFA, that indicates that the subsequence of the read exactly matches a primer sequence corresponding to the except state. Exact matches may be identified by the exact match module 220.

At 610, an approximate location of a primer sequence may be identified by comparing a first hash of the primer sequence to a second hash of a subsequence of a one of the plurality of reads. The hashes may be performed by any of the techniques described above. For example, the first hash and the second hash may be computed by counting a number of k-mers (e.g., 3-mers, 4-mers, 5-mers, etc.) within the primer sequence and the read respectively. The k-mers may be embedded into $4^k$ dimensional a vector space. This technique for creating and comparing hashes is shown in FIGS. 3 and 4. The hashing module 216 may perform some or all of the operations to find approximate locations of a primer sequence.

At 612, an exact location for the primer sequence may be identified by finding a subsequence in the approximate location from 610 having a smallest edit distance from the primer sequence. The edit distance may be calculated by a minimum number of insertions, deletions, and substitutions to transform the subsequence of the read into the primer sequence. The edit distance module 218 may be used to calculate the edit distance. Identifying the exact location of the primer sequence may include sliding a window for comparison one nucleotide per iteration along the approximate location in the read and identifying alignment of the window with respect to the approximate location that has an edit distance to the primer sequence that is smaller than any other alignment. This technique for identifying an exact location in a read is illustrated in FIG. 5.

At 614, payload regions are extracted from the plurality of reads. The payload regions are subsequences of the reads that contain information corresponding to the original data included in the polynucleotide molecules. The payload regions may be extracted by distinguishing portions of the reads that correspond to the payload regions and portions of the reads that correspond to other polynucleotide sequences. In an implementation, the payloads in the polynucleotide molecules may be located between two primer sequences. Thus, once the primer sequences are identified in the reads, the portion of the reads in between two primer sequences may be identified as a payload region. In an implementation, payload regions may only be identified as payload regions if located between two paired primer sequences. Extracting may include storing the subsequence of the reads that corresponds to the payload regions in a separate location, with a separate identifier, or another manner that can be distinguished from the remainder of the sequence data contained in the reads. Extraction of the reads may include grouping or clustering the extracted reads based on the surrounding primer sequences. Thus, extracted payloads that were located between the same pair of primer sequences may be grouped with each other as part of the extraction. A cluster of payloads may be the same or similar to the clustered payload sequences 126 shown in FIG. 1. Extraction of payload regions may be performed by the payload extraction module 124.

At 616, the clustered payload may be decoded, for example, by converting the sequence of nucleotide bases to binary data and returning the binary data to its original structure such as, for example, the decoded computer file 128.

Figure 7:
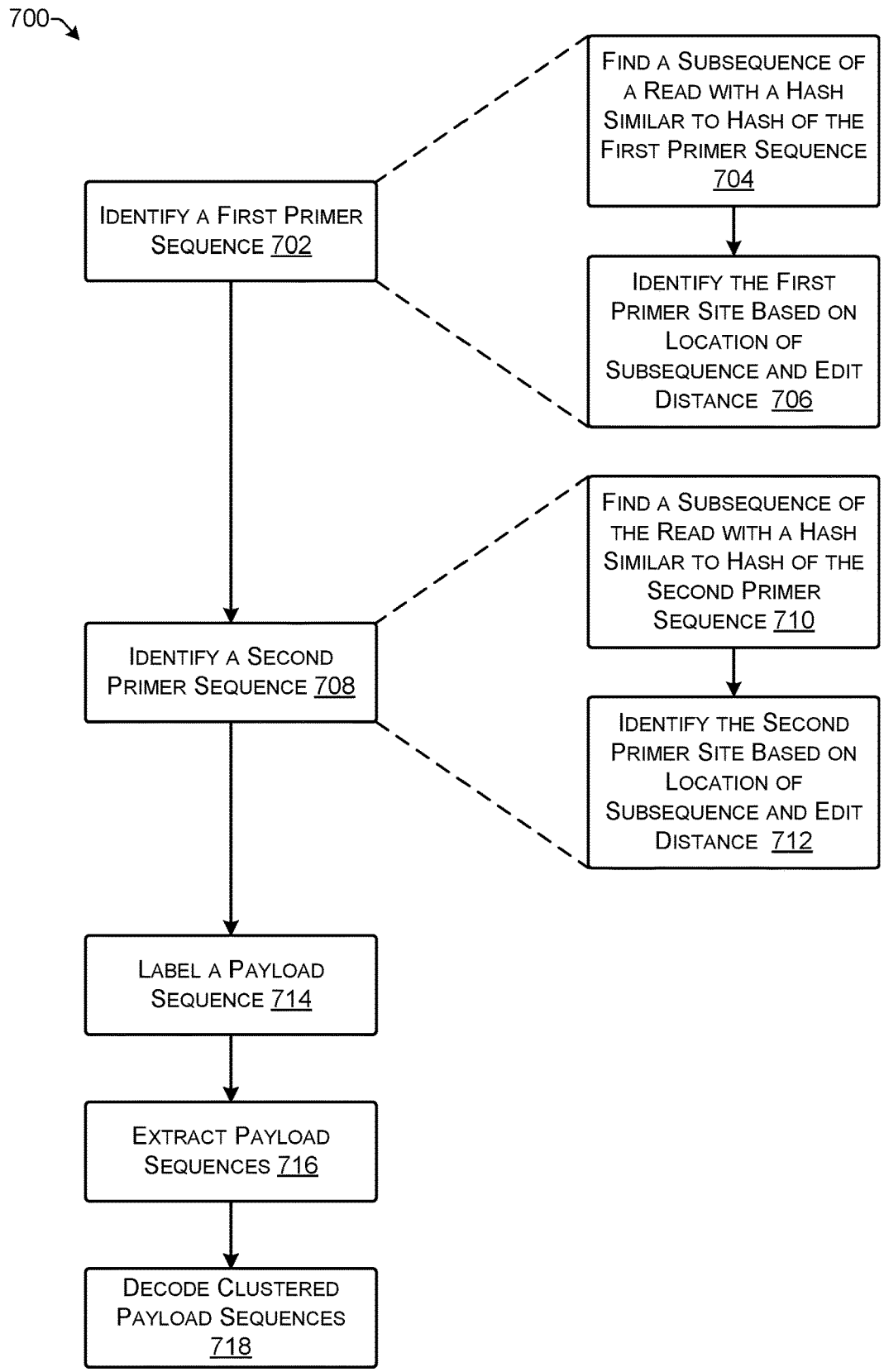
FIG. 7 illustrates a flow diagram of a technique for labeling a payload sequence based on a first primer sequence and a second primer sequence.

FIG. 7 shows process 700 for labeling a payload sequence based on a first and second primer sequence. The process 700 may be implemented in whole or part by the computing device 202 shown in FIG. 2.

At 702, a first primer sequence corresponding to a forward primer is identified in a polynucleotide read that was generated by a polynucleotide sequencer. The polynucleotide read may one of the polynucleotide reads 122 introduced in FIG. 1. Thus, the polynucleotide read may encode information that results part of an original source of data such as the binary data 104.

At 704, the first primer sequence may be identified in part by finding a location of a first subsequence of the polynucleotide read for which a first hash is less than a threshold distance from a hash of the primer sequence. The hash functions may be any of those described above. For example, the hash of a subsequence of the polynucleotide read may be a vector in $4^k$ dimensional space indexed by k-mers such that the t-th coordinate of the hash equals a number of occurrences of t in the first subsequence of the polynucleotide read. The hash of the primer sequence may be calculated in the same way.

A distance between the two hashes may be determined by an $L_1$ distance, a Hamming distance, a number of positions in the hashes for which one of the hashes has a zero value and the other hash has a non-zero value, or by any other suitable technique. The threshold distance from the hash of the first primer sequence to the hash of the first subsequence of the polynucleotide read may be established in any of the ways described above. When the distance between two hashes is less than the threshold distance, those two hashes are considered to be potential matches which may be further evaluated by edit distance calculations. The hashes and comparison of the hashes may be performed by the hashing module 216.

At 706, the first primer sequence may be more precisely identified based on location of the first subsequence of the polynucleotide found at 704 and a first edit distance from the first primer sequence. Identifying the location of the first primer sequence may include finding a subsequence of the polynucleotide read such that the first edit distance to the first primer is minimized. The edit distance may be evaluated over the evaluation window it is a portion of the polynucleotide read that includes and is longer than the first subsequence of the polynucleotide read identified at 704. The edit distance may be calculated by dynamic programming that recursively evaluates multiple partially overlapping subsequences in the evaluation window. FIG. 5 provides one illustration of this technique for edit distance calculation. Edit distance calculations may be performed using any of the techniques described above and may be implemented by the edit distance module 218.

At 708, a second primer sequence corresponding to a reverse primer is identified in the polynucleotide read. The reverse primer may be paired with the forward primer from 702. Pairing of the primers indicates that use of the forward primer and the reverse primer together during PCR may result in amplification of the polynucleotide sequence between the corresponding primers.

At 710, the second primer sequence may be identified in part by finding a location of a second subsequence of the polynucleotide read for which a second hash is less than the threshold distance from a hash of the second primer sequence. Hashing of the second subsequence of the polynucleotide read may be performed by the same techniques used at 704.

At 712, the second primer sequence may be more precisely identified based on location of the second subsequence of the polynucleotide found at 710 and a second edit distance from the second primer sequence. The edit distance may be calculated by the same techniques used at 706.

At 714, a third subsequence of the polynucleotide read located between the first primer sequence and the second primer sequence is labeled as a payload sequence. This payload sequence may be associated with the forward primer and the reverse primer that correspond to the first primer sequence and the second primer sequence respectively. The payload sequence may be adjacent to an end of the first primer sequence and adjacent to an end of the second primer sequence. One possible configuration is for the payload sequence to be located between the two primer sequences as illustrated in FIG. 1. Association with the forward primer and the reverse primer makes it possible to identify the source of the data contained in the payload sequence. Identification of the payload sequence and separation from other sequences contained in a polynucleotide read may be performed by the payload extraction module 124.

At 716, the payload sequence is extracted together with the plurality of other payload sequences that are also associated with the forward primer and the reverse primer. Clustering the extracted payload sequences may create a set of clustered payload sequences 126 as shown in FIG. 1. Assuming a unique correspondence between the primers and the original source of the data, extracting the payloads based on the associated primers groups all payloads containing a portion of the original source data together.

At 718, the payload sequence and other payload sequences clustered together are decoded to generate the original source data which may be a computer file such as the decoded computer file 128.

EXAMPLES

The follow examples illustrate differences in computational expense as represented by running time between multiple techniques for extracting payload sequences from a plurality of noisy reads. All results in this example were computed on a Surface Book i7 equipped with Intel® Core™ i7-7700K CPU @ 4.20 GHz 4 cores with 8 logical processor, 16 GB of RAM, dGPU device, a 1 TB solid-state drive, running Linux subsystem for Windows 10.

In the first example, three different techniques were used to identify and cluster payload sequences from a set of 1,187,000 DNA reads generated by Nanopore sequencing. The first technique used naïve edit distance calculations to identify subsequences within the set of DNA reads that have class threshold distance from any one of the primer sequences. Thus, edit distance calculations were performed for each subsequence of each read of length 20, which is the length of the primer sequences. Edit distance calculations were performed from each of these subsequences to each of 50 different primer sequences. This was the most computationally expensive technique attempted and took 375 minutes to extract the payload sequences.

The next technique, referred to as focused edit distance, limited the number of edit distance calculations perform by first identifying evaluation windows with in the DNA reads based on comparison of hash values as described above. Within the evaluation windows, naïve edit distance calculations were performed between each subsequence of length 20 and the specific primer sequence used to identify the evaluation window. Thus, the edit distance calculations were performed using the same technique as in the prior approach, but the number of edit distance calculations performed was limited both in terms of the length of the DNA reads evaluated and the target primer sequences searched. With this modification, clustering the payload sequences took 48 minutes—a decrease of over 87%.

The third technique, referred to as recursive edit distance, is similar to the focused edit distance technique but modifies that procedure by recursively calculating edit distances within the evaluation windows using the specific distance techniques described above. Thus, rather than performing naïve edit distance calculations over a limited portion of the DNA reads, the edit distance calculations performed over the evaluation windows recursively calculate edit distance values nucleotide by nucleotide to identify a single subsequence within each evaluation window that has the minimum edit distance to the target primer sequence. This further modification reduces the running time to 10 minutes which is less than a quarter of the time used by the focused edit distance technique and only 2.7% of the time used by the naïve edit distance technique. A comparison of these results is shown in Table 1 below.

TABLE 1

Improvements in Running Time

| Technique | Running Time (minutes) |
| --- | --- |
| Naïve edit distance | 375 |
| Focused edit distance | 48 |
| Recursive edit distance | 10 |

In a second example, the same set of DNA reads generated by Nanopore sequencing was processed in its entirety and two smaller random subsets of 111,000 reads and of 14,000 reads each. In this example the primer length was 20 bp and there were 10 different primers. The total strand length of the reads was 110 bp.

An alternative technique for aligning sequences was tested by using the well-known Basic Local Alignment Search Tool (BLAST) algorithm to align primer sequences to the reads. This was by far the slowest technique taking over five hours to process the entire dataset. The "naïve edit distance" technique use edit distance along the entire length of the reads to location matches for the primer sequences. However, this technique was not entirely "naïve" in that it used heuristics to find likely locations for a second primer sequence once a first was identified. The naïve edit distance technique was much faster than BLAST for all dataset sizes.

The focused edit distance technique was the same as described above in the first example. Using initial hash comparison to focus the edit distance calculations to limited evaluation windows reduced the running time by over 90% for all datasets.

The recursive edit distance technique shown in Table 2 is the same as described in the example above. Applying edit distance calculations recursively across the evaluation windows rather than calculating each edit distance anew further improved running time. This technique is less computationally intensive than any of the other techniques as evidenced by the shorter running time. The advantage of calculating edit distances recursively increased as the dataset size increase. Thus, the recursive edit distance technique is likely to be markedly faster than the focused edit distance technique on the very large datasets present in real-world applications.

The effect of using additional processor cores was also considered. The naïve edit distance, focused edit distance, and first run of the recursive edit distance techniques (single core) were all performed using only one processor core. The technique using recursive edit distances (multiple cores) was also performed using all the cores of the Surface Book. Use of multiple cores reduced the running time by about two-thirds.

TABLE 2

Comparison over different sizes of datasets

| Technique | Running Time (seconds) | Dataset Size (1000s of reads) |
|---|---|---|
| BLAST | 19,320 | 1,173 |
| Naïve edit distance (single core) | 1,615 | 1,187 |
| Focused edit distance (single core) | 112 | 1,187 |
| Recursive edit distance (single core) | 77 | 1,187 |
| Recursive edit distance (multiple cores) | 22 | 1,187 |
| BLAST | 309 | 125 |
| Naïve edit distance (single core) | 144 | 111 |
| Focused edit distance (single core) | 10 | 111 |
| Recursive edit distance (single core) | 7 | 111 |
| Recursive edit distance (multiple cores) | 2 | 111 |
| BLAST | 40 | 14 |
| Naïve edit distance (single core) | 27 | 14 |
| Focused edit distance (single core) | 2 | 14 |
| Recursive edit distance (single core) | 1.5 | 14 |
| Recursive edit distance (multiple cores) | 0.5 | 14 |

Thus, the techniques presented in this disclosure provide improvement in the functioning of a computing device tasked with extracting payload regions from a set of noisy polynucleotide reads.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A system comprising:
one or more processing units;
one or more computer-readable media in communication with the one or more processing units;
a hashing module stored in the one or more computer-readable media and executable on the one or more processing units to generate a first hash of a primer sequence, generate a second hash of a subsequence of a read produced by a polynucleotide sequencer, and determine that the second hash has less than a threshold difference from the first hash; and
an edit distance module stored in the one or more computer-readable media and executable on the one or more processing units to identify an evaluation window in the read which includes and is longer than the subsequence of the read and determine a best-match subsequence within the evaluation window that is a same length as the primer sequence and that has a smallest edit distance from the primer sequence relative to other subsequences within the evaluation window.

Clause 2. The system of clause 1, wherein the hashing module generates the first hash by encoding k-mers present in the primer sequence as a first vector, generates the second hash by encoding k-mers present in the read as a second vector, and the threshold difference is a threshold distance from the first vector to the second vector.

Clause 3. The system of any of clauses 1-2, wherein a distance from the first vector to the second vector is calculated by an $L_1$ distance.

Clause 4. The system of any of clauses 1-2, wherein a distance from the first vector to the second vector is calculated by a Hamming distance.

Clause 5. The system of any of clauses 1-2, wherein a distance from the first vector to the second vector is calculated by a number of positions that are zero in the first vector but non-zero in the second vector.

Clause 6. The system of any of clauses 1-5, wherein the edit distance module uses dynamic programming to identify the best-match subsequence by recursively calculating edit distances for subsequences the same length as the primer sequence within the evaluation window by advancing a region of comparison one base pair per iteration.

Clause 7. The system of any of clauses 1-6, further comprising a payload extraction module stored in the one or more computer-readable media and executable on the one or more processing units to separate a payload region of the read from other sequences in the read.

Clause 8. The system of any of clauses 1-7, further comprising an exact match module stored in the one or more computer-readable media and executable on the one or more processing units to identify an exact match between the primer sequence and a subsequence of the read by determining that the subsequence of the read has an edit distance of zero from the primer sequence.

Clause 9. The system of any of clauses 1-7, further comprising an exact match module stored in the one or more computer-readable media and executable on the one or more processing units to identify an exact match between the primer sequence and a subsequence of the read by building a deterministic finite automaton (DFA) having an accept state representing the primer sequence.

Clause 10. The system of any of clauses 1-9, further comprising a primer location prediction module stored in the one or more computer-readable media and executable on the one or more processing units to predict a location of the primer sequence in the read based on a known length of a payload region and a different location of a different primer sequence.

Clause 11. The system of any of clauses 1-9, further comprising a primer location prediction module stored in the one or more computer-readable media and executable on the one or more processing units to predict a location of the primer sequence in the read based on an offset from a start of the read, the offset based on sequencing technology used by the polynucleotide sequencer.

Clause 12. The system of any of clauses 1-9, further comprising a primer location prediction module stored in the one or more computer-readable media and executable on the one or more processing units to predict a location of the primer sequence in the read based on a known sequence of an additional primer that is paired with the primer sequence.

Clause 13. A method comprising:
receiving a plurality of reads from a polynucleotide sequencer;
receiving a plurality of primer sequences;
locating primer sequences within the plurality of reads; and
extracting payload regions from the plurality of reads, the payload regions located between two primer sequences, such that payload regions associated with a same pair of primers are grouped together.

Clause 14. The method of clause 13, wherein the locating primer sequences comprises:
identifying an approximate location by comparing a first hash of a one of the primer sequences to a second hash of a first subsequence of a one of the plurality of reads; and
identifying an exact location by finding a second subsequence in the approximate location having a smallest edit distance from the one of the primer sequences.

Clause 15. The method of clause 14, wherein the first hash and the second hash are computed by counting a number of k-mers within the one of the primer sequences and the first subsequence of the one of the plurality of reads respectively.

Clause 16. The method of any of clauses 14-15, wherein identifying the exact location comprises:
sliding a window for comparison one nucleotide per iteration along the approximate location; and
identifying an alignment of the window with respect to the approximate location that has an edit distance to the one of the primer sequences that is smaller than any other alignment.

Clause 17. The method of any of clauses 13-16, wherein the locating primer sequences comprises finding exact matches between subsequences of the reads and the primer sequences by identifying subsequences of the reads that have an edit distance of zero from one of the primer sequences.

Clause 18. The method of any of clauses 13-16, wherein the locating primer sequences comprises finding exact matches between subsequences of the reads and the primer sequences by building a deterministic finite automaton (DFA) having accept states representing the primer sequences.

Clause 19. Computer-readable media storing instructions that when executed by one or more processing units performing the method of any of clauses 13-18.

Clause 20. A system comprising one or more processing units and one or more computer-readable media in communication with the one or more processing units, the system configured to perform the method of any of clauses 13-18.

Clause 21. A method comprising:
identifying, in a polynucleotide read generated by a polynucleotide sequencer, a first primer sequence and a second primer sequence, the identifying performed by:
finding a first location of a first subsequence of the polynucleotide read for which a first subsequence hash is less than a threshold distance from a first primer hash of the first primer sequence;
identifying the first primer sequence in the polynucleotide read based on the first location of the first subsequence of the polynucleotide read and a first edit distance from the first primer sequence;
finding a second location of a second subsequence of the polynucleotide read for which a second subsequence hash is less than the threshold distance from a second primer hash of the second primer sequence; and
identifying the second primer sequence in the polynucleotide read based on the location of the second subsequence of the polynucleotide read and a second edit distance from the second primer sequence;
labeling a third subsequence of the polynucleotide read between the first primer sequence and the second primer sequence as a payload sequence; and
extracting the payload sequence together with a plurality of other payload sequences also associated with the first primer and the second primer.

Clause 22. The method of clause 21, wherein the first subsequence hash is a vector in $4^k$ dimensional space indexed by k-mers such that the t-th coordinate of the first subsequence hash equals a number of occurrences of t in the first subsequence of the polynucleotide read.

Clause 23. The method of any of clauses 21-22, wherein the threshold distance from the first primer hash to the first subsequence hash is determined by an $L_1$ distance.

Clause 24. The method of any of clauses 21-22, wherein the threshold distance from the first primer hash to the first subsequence hash is determined by a Hamming distance.

Clause 25. The method of any of clauses 21-22, wherein the threshold distance from the first primer hash to the first subsequence hash is determined by a number of positions in the first subsequence hash and the first primer hash for which one of the hashes has a zero value and the other hash has a non-zero value.

Clause 26. The method of any of clauses 21-25, wherein identifying the first primer sequence further comprises finding a subsequence of the polynucleotide read such that the first edit distance to the first primer is minimized.

Clause 27. The method of any of clauses 21-26, wherein the payload sequence is adjacent to an end of the first primer sequence and adjacent to an end of the second primer sequence.

Clause 28. The method of any of clauses 21-27, wherein identifying the first primer sequence further comprises evaluating the first edit distance over an evaluation window which is a portion of the polynucleotide read that includes and is longer than the first subsequence of the polynucleotide read.

Clause 29. The method of clause 28, wherein the first edit distance is calculated by dynamic programming that recursively evaluates multiple partially overlapping subsequences in the evaluation window.

Clause 30. The method of any of clauses 21-29, further comprising decoding the payload sequence and the other payload sequences to generate a computer file.

Clause 31. Computer-readable media store instructions that when executed by one or more processing units performing the method of any of clauses 21-30.

Clause 32. A system comprising one or more processing units and one or more computer-readable media in communication with the one or more processing units, the system configured to perform the method of any of clauses 21-30.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that it discloses.

The invention claimed is:

1. A computer-implemented method comprising:
identifying, in a polynucleotide read generated by a polynucleotide sequencer, a first primer sequence and a second primer sequence, the identifying performed by:
creating hashes of a plurality of primer sequences; creating rolling hashes from the polynucleotide read; calculating a distance between a first hash of the polynucleotide read and a hash of each of the plurality of primer sequences, then determining a distance between subsequent hashes of the polynucleotide read and the hash of each of the plurality of primer sequences by updating the distance without calculating the distance anew; finding a first location of a first subsequence of the polynucleotide read for which a first subsequence hash that is one of the rolling hashes is less than a threshold distance from a first primer hash of the first primer sequence that is a hash of one of the plurality of primer sequences;
identifying the first primer sequence in the polynucleotide read based on the first location of the first subsequence of the polynucleotide read and a first edit distance from the first primer sequence;
finding a second location of a second subsequence of the polynucleotide read for which a second subsequence hash that is one of the rolling hashes is less than the threshold distance from a second primer hash of the second primer sequence that is it hash of one of the plurality of primer sequences; and
identifying the second primer sequence in the polynucleotide read based on the location of the second subsequence of the polynucleotide read and a second edit distance from the second primer sequence;
labeling a third subsequence of the polynucleotide read between the first primer sequence and the second primer sequence as a payload sequence;
extracting the payload sequence together with a plurality of other payload sequences also associated with the first primer sequence and the second primer sequence, wherein the payload sequence encodes binary data; and
decoding the payload sequence and the other payload sequences to generate a computer file.

2. The method of claim 1, wherein the first subsequence hash is a vector in $4^k$ dimensional space indexed by k-mers such that a t-th coordinate of the first subsequence hash equals a number of occurrences of t in the first subsequence of the polynucleotide read.

3. The method of claim 1, wherein the threshold distance from the first primer hash to the first subsequence hash is determined by an $L_1$ distance.

4. The method of claim 1, wherein identifying the first primer sequence further comprises finding a subsequence of the polynucleotide read such that the first edit distance to the first primer sequence is minimized.

5. The method of claim 1, wherein the payload sequence is adjacent to an end of the first primer sequence and adjacent to an end of the second primer sequence.

6. The method of claim 1, wherein identifying the first primer sequence further comprises evaluating the first edit distance over an evaluation window which is a portion of the polynucleotide read that includes and is longer than the first subsequence of the polynucleotide read.

7. The method of claim 6, wherein the first edit distance is calculated by dynamic programming that recursively evaluates multiple partially overlapping subsequences in the evaluation window.

8. The method of claim 1, wherein the polynucleotide read is a read of a synthetic polynucleotide molecule designed so that the first primer sequence and the second primer sequence flank the payload region.

9. The method of claim 1, wherein the threshold distance from the first primer hash to the first subsequence hash is determined by a Hamming distance.

10. The method of claim 1, wherein the first primer hash and the first subsequence hash are vectors generated by k-mer embedding such that the vectors are strings of integers each integer representing a number of instances of a k-mer in the respective hash and wherein the threshold distance from the first primer hash to the first subsequence hash is determined by a number of positions in the first subsequence hash and the first primer hash for which one of the hashes has a zero value and the other hash has a non-zero value.

* * * * *